US010787678B1

(12) United States Patent
Adang et al.

(10) Patent No.: US 10,787,678 B1
(45) Date of Patent: Sep. 29, 2020

(54) CADHERIN FRAGMENTS FOR MANAGING INSECT RESISTANCE TO CRY PROTEINS

(71) Applicant: University of Georgia Research Foundation, Inc., Athens, GA (US)

(72) Inventors: Michael J. Adang, Athens, GA (US); Gang Hua, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 112 days.

(21) Appl. No.: 15/426,000

(22) Filed: Feb. 6, 2017

Related U.S. Application Data

(62) Division of application No. 14/072,619, filed on Nov. 5, 2013, now abandoned.

(60) Provisional application No. 61/722,592, filed on Nov. 5, 2012.

(51) Int. Cl.
*C07K 14/325* (2006.01)
*C12N 15/82* (2006.01)
*C07K 14/435* (2006.01)
*A01N 63/10* (2020.01)

(52) U.S. Cl.
CPC ......... *C12N 15/8286* (2013.01); *A01N 63/10* (2020.01); *C07K 14/325* (2013.01); *C07K 14/43563* (2013.01)

(58) Field of Classification Search
None
See application file for complete search history.

(56) References Cited

U.S. PATENT DOCUMENTS

| 4,797,368 | A | 1/1989 | Carter et al. |
| 6,551,962 | B1 | 4/2003 | Pershing et al. |
| 8,486,887 | B2 | 7/2013 | Adang et al. |
| 2005/0283857 | A1 | 12/2005 | Adang et al. |
| 2011/0183896 | A1 | 7/2011 | Adang et al. |
| 2011/0201549 | A1 | 8/2011 | Adang |

OTHER PUBLICATIONS

Fabrick et al. ('A novel Tenebrio molitor cadherin is a functional receptor for Bacillus thuringiensis Cry3Aa toxin' Journal of Biological Chemistry v284(27) 2009 pp. 18401-18410) (Year: 2009).*
Tabashnik et al ('Insect resistance to Bt crops: lessons from the first billion acres' Nature Biotechnology v31(6) Jun. 2013 pp. 510-521).
Chen, J., Hua, G., Jurat-Fuentes, J.L., Abdullah, M.A., Adang, M.J., 2007. Synergism of Bacillus thuringiensis toxins by a fragment of a toxin-binding cadherin. Proc. Natl. Acad. Sci. U. S. A. 104, 13901-13906.
Park, Y., Abdullah, M.A., Taylor, M.D., Rahman, K., Adang, M.J., 2009. Enhancement of Bacillus thuringiensis Cry3Aa and Cry3Bb toxicities to coleopteran larvae by a toxin-binding fragment of an insect cadherin. Appl. Environ. Microbiol. 75, 3086-3092.
Sayed, et al., A novel cadherin-like gene from western corn rootworm, Diabrotica virgifera virgifera (Coleoptera : Chrysomelidae), larval midgut tissue, Oct. 2007, Insect Molecular Biology, vol. 16, NR. 5, XP002593307.
Siegfried, et al., Expressed sequence tags from Diabrotica virgifera virgifera midgut identity a coleopteran cadherin and a diversity of cathepsins, Insect Molecular Biology 2005, p. 137-143.
UniProt entry Q5MK05, Uniprot (online), Jul. 22, 2005 [retrieved on Dec. 4, 2009] Retrieved from the internet, URL: http://www.uniprot.org/uniprot/Q5MK05.txt?version=20>.
Gao, Y.L., Jurat-Fuentes, J.L., Oppert, B., Fabrick, J.A., Liu, C.X., Gao, J.H., Leia, Z., 2011. Increased toxicity of Bacillus thuringiensis Cry3Aa against Crioceris quatuordecimpunctata, Phaedon brassicae and Colaphellus bowringi by a Tenebrio molitor cadherin fragment. Pest Manag. Sci. 67, 1076-1081.
Bravo, A., Likitvivatanavong, S., Gill, S.S., Soberón, M., 2011. Bacillus thuringiensis: A story of a successful bioinsecticide. Insect Biochem. Mol. Biol. 41, 423-431.

* cited by examiner

Primary Examiner — Ronald T Niebauer
(74) Attorney, Agent, or Firm — Faegre Drinker Biddle & Reath, LLP

(57) ABSTRACT

The subject invention relates in part to a combination of a cadherin peptide derived from *Alphitobius diaperinus* and a Cry protein capable of inhibiting an insect. In certain embodiments, the combination is capable of overcoming Cry protein resistance in insects that are resistant to the Cry protein alone.

10 Claims, 5 Drawing Sheets

Specification includes a Sequence Listing.

SEQUENCE LISTING

```
<160> NUMBER OF SEQ ID NOS: 54

<210> SEQ ID NO 1
<211> LENGTH: 5022
<212> TYPE: DNA
<213> ORGANISM: Alphitobius diaperinus

<400> SEQUENCE: 1
atgaagctca ggtgtttggt tttttgggga cttttctgtt atggtgtcgc attcaaattc      60
gaagacgcca atcaatctga tgtaacattt ggtggtaaca caacatcagg agcacgacaa     120
atttttgtaa aggaaaaaaa tgtgaacaag aatggcacaa cagacagaat taacattgtt     180
ttaataactg aagttgacgc tgaaatgact gtatcaggga atacctaccc gaatcaattc     240
gatgtaaaaa ttctggatgg tagcaaaaaa agtgaaaagt atgttgaagt gaatcgtgtg     300
gattacgaag ccttaggaac tcaaaccact tttcctatag atattatttc aaataatgat     360
atcggtacca aacaaagtat aagtctgact attgaaaata ttgatgatga gagcccaact     420
ttgtctacta ataataattg tatactggat gaaaacacta aatatctcat tgatgatgtc     480
tctaacaatc cttgctcatt tgaaatccaa gatcccgacg ggtatttgaa tacaatggat     540
tttacgggaa ttacaggaga gaatggagaa agtgatttat tcgaattcca atacaaggaa     600
attcctaaaa acaacaccta tggagctgag gtttatctga cactgaaaaa tgataaaact     660
ctagattacg aaagtaaaac tctttatata tttcacgtag aagcaaagga tggggcggga     720
```

| | |
|---|---|
| catccgacta gcccagtttc cagtgtgcca attattgttc aggtgaacga tcagccagat | 780 |
| gaaaacccag tctgggacag ttctttcaga tcggctatta gtatagttga agaaagtgag | 840 |
| acgacaataa ctgtatctgc aaaagatgga gactacggca tcaacaacaa gatcaattat | 900 |
| aagatcgaat ttacaaattt gaatatgtca ccttcttcag acgattcaga cctgattacc | 960 |
| atagatccag aaaccggcgt aattacgatt aataaaattg atagagaaaa aggttataag | 1020 |
| gatgaccaag tcattttga tgtgactgct tttgaagtgc ctgatcccag tgcaaaaata | 1080 |
| acagaccaag tgactctcat cattcaggat attgatgata acataccaga gatcactacg | 1140 |
| aaagatggct ctaaaccatt gcagatccaa gtccccgaaa acactgctga cttaggtgaa | 1200 |
| ctagacatta cggtttcaga cattgatacg ggagaaaacg cactttacac agcagaactc | 1260 |
| aaaccaattg gcgatgtaga tcacacaact gctttagca tagtacctgg aaggggtac | 1320 |
| gaaactacta cacttattct cacagtgact gattctacta agctcgatta cgaagatatt | 1380 |
| gagtggaggg aaatacaatt gaagttagaa actactggca ctaaaaatcc atcacaaaca | 1440 |
| gatactttaa atattaccat taccttacaa gaccttaacg atgaaagtcc tatatttgaa | 1500 |
| cctactgaag ctgaagttaa tatcaaagaa actgtaacta aaggtataac aatttataat | 1560 |
| attatagcaa ctgatgcgga cgcagtggat gccaaattaa agcacaccat ttcgagcaaa | 1620 |
| tctgcagcca ctatttgac cattgaggaa tttggtggaa acgtaactac tatagcagat | 1680 |
| agtgcattcg atttgaaaa gcaggagcag ctgattgtac agattcaagc tgaagatagc | 1740 |
| gctgctccta ctccgcatac aaaactcttt cagttaacta tcaatgtttt agatgttaac | 1800 |
| gacgagaaac ccacactcaa agtagggtct acgattaagg tgaatgaaaa ccaagaagat | 1860 |
| ggtgcctcac tcgaagcgga tatttctgct acagatcctg atactacggc agaattggag | 1920 |
| ttttcgatcg attggaccaa atcttatgcc acaaaaaaat ctcaaagaat aaaggatgaa | 1980 |
| gtatttgcag actacaattg cattaaggtt gaaactgaac tagtagaaaa cggaaaacga | 2040 |
| aatcaagtta aagccaagtt aactatcatt gagactcaaa gaaacaacac tccggattat | 2100 |
| gaaactttg ataacttgta cattgctttg atagtaacag ataacaatac ggaagtctcc | 2160 |
| ggacaagaaa gtgattccgc tacggtcgtt atttccattg gggatcttaa cgacaatgcc | 2220 |
| cccaaattcg ctgatgacac cgctactgct actagacggg taccggaaaa agctgttgac | 2280 |
| ggcacactca tcacgactgt tgtcgccact gacgatgatt taggaaccaa attgaactat | 2340 |
| tccatagaaa gagccgataa agatacacca ttgtgggtta gcatcgacga aacttccggt | 2400 |
| gctattagtg ttcatttgga aaaaatgaa gaaattgact gcgatgatcc tccaagagat | 2460 |
| gatttaaaat atattgttac cgtcactgat ggcaaataca atgatactgc tactatcaca | 2520 |
| attggtattg atgatgaaaa tgagaataaa ccgactgttc agaatgtaac tgttacaaca | 2580 |
| ttgcaagaac aagacgaaca gtcgcaggat gattctagtc ccaatggcaa aatcgttgct | 2640 |
| gagataaagt acaccgacat tgatagagat gctgaatata aaaagtcag ttgtggattc | 2700 |
| gcttcctcaa cgacgagtga cgttaccaac agatttgata ttgttaataa tacaattaaa | 2760 |
| gtgaagcttg aggatggata cgatttagat agagaaaaaa atcctacctt cacatttgaa | 2820 |
| ctgaattgtg ttgacaatcc cacaaagcaa ggtagcggta tttctaatgc agcggagagc | 2880 |
| ataccaaaag tcttcatcgc cctacaagac attaacgata agagacccat cattacaaac | 2940 |
| caggatatta aggaataga cgaaagcaca tcaggttcaa ttggtactca acttatagga | 3000 |
| aaagatgaag atgaaagcaa gaatggtcag atccactata atggtataac agcaatcaaa | 3060 |

```
agatacatca atgagaatga cgctagtcca gtggacgatc ctcctcaaga tctcatcaaa    3120
gtggaagatg ccggagacga caaaaatgcc aatttaacaa tcactgcgga gaatttggaa    3180
aattattacg gatatctcaa actgaatatt agctttaccg ataagggaga ttctcctctg    3240
gtcaacgaag aagtagtaac tttagaagtc gccaaatata atttcaaaga gccaaccttc    3300
acttttccaa cacaaggcaa atcaattttc ttacaaaaaa gtcaagagcc taacagcaga    3360
ctttatttat tcaacggaga agctctcgag gattttgtag tggatgatgg acaaaagggg    3420
aaattttcgt tcaactataa ggttttggat gcaagcgtaa cgggaatatt aatatgaaa    3480 aataatcaac ttcaaattat taatgccgca tatgataccg aaatgatata caagctaacg    3540
gttgaagcaa gtataaagga acaaacgcaa ataaatggta acccactttt tgcaaggtgc    3600
gaatttaacg tcgggttctt cgataaagat aacaccgatc caatcttcaa aaataaacac    3660
gaagatactc atgaaatggc tgaggaagat gatacattgt tttatgtact gatagaaaat    3720
gcaacctacg ccaaagaaga tgttcctgac gatttaagca cattttattt gttagcagaa    3780
ggagagaggg atattttcga tgttgacaaa ttcactggaa aagtcacttt gaataaacca    3840
ttggattatg aaaccaaaaa aagccacagc ttgacgatac agtcatctaa ttctgataag    3900
ttgaaactaa atgccagtga agagacgaaa ttacatctaa ccatcattgt gacagatatt    3960
aacgaccatg ctcctgtaat ggattccgat tcttacatta cagtattacc attagtggac    4020
gcagtctcga ctgcaaaatt ggtgacaata cacgctacag atccagatga cacaagcgaa    4080
gtgcagtatc agattgaatc ctgcattggc tctggagatc ttttacaaaa gctatgtggc    4140
aataatccct ttgaaataaa taaaattagt ggtgaaattt ccgctcagat tcaatcagcg    4200
aatcttagta aatgggatgg tcatttcaat ttaacagtta cagcggccga tgaggctggt    4260
ttcgatgaca aaaatcacac agacgaagca gttgtgacac tatatctcgt cacaaaacta    4320
catcttgtag catttgattt tgaaaatagc ttagaacaag ttcaaaataa aagtaacgaa    4380
atcaaaacaa tcctcgatga acaatttgct gaaacttctg atggtggaac accatacgta    4440
gccactgtac aaggcgcaaa cgctaaatcc gatgaaatta acagcaac cgtatatttt    4500 ctgaatctta acaacagaa accagtaaat aaagataata tatacagtta ttgtactaac    4560
actcagtatt tcggaagtat gagatcagct ttcttagcag agggtttatc attaatgagt    4620
tttgacggaa cctctaacga aactgaagat atggaggaga ttttaacggc ctggcttatt    4680
ggagtttcgg tcgttcttgg agctttgtgt attattcttt ccattgcgtt catcctaaaa    4740
acaagaagtc tgaatcaacg catcgataaa ctttctagca ctaagttcgg ttcacaagaa    4800
tcagggttga acagaacagg agtggcagct cctaccacta caaacatgc tgttgagggc    4860 tcaaatccgg tttataacaa tgaagtagat actaacgaag tagatcggag agtgagtgtg    4920
gctagtggag gttccgagtt gattggcata gaagatgacg ataaattcaa ctataatagc    4980
tatccaacca aagatgaaga aaatgcagaa gaagagaatt aa                     5022
```

<210> SEQ ID NO 2
<211> LENGTH: 1673
<212> TYPE: PRT
<213> ORGANISM: Alphitobius diaperinus

<400> SEQUENCE: 2

Met Lys Leu Arg Cys Leu Val Phe Trp Gly Leu Phe Cys Tyr Gly Val
1               5                   10                  15

Ala Phe Lys Phe Glu Asp Ala Asn Gln Ser Asp Val Thr Phe Gly Gly
            20                  25                  30

```
Asn Thr Thr Ser Gly Ala Arg Gln Ile Phe Val Lys Glu Lys Asn Val
             35                  40                  45

Asn Lys Asn Gly Thr Thr Asp Arg Ile Asn Ile Val Leu Ile Thr Glu
 50                  55                  60

Val Asp Ala Glu Met Thr Val Ser Gly Asn Thr Tyr Pro Asn Gln Phe
 65                  70                  75                  80

Asp Val Lys Ile Leu Asp Gly Ser Lys Ser Glu Lys Tyr Val Glu
                 85                  90                  95

Val Asn Arg Val Asp Tyr Glu Ala Leu Gly Thr Gln Thr Thr Phe Pro
             100                 105                 110

Ile Asp Ile Ile Ser Asn Asn Asp Ile Gly Thr Lys Gln Ser Ile Ser
             115                 120                 125

Leu Thr Ile Glu Asn Ile Asp Asp Glu Ser Pro Thr Leu Ser Thr Asn
             130                 135                 140

Asn Asn Cys Ile Leu Asp Glu Asn Thr Lys Tyr Leu Ile Asp Asp Val
145                 150                 155                 160

Ser Asn Asn Pro Cys Ser Phe Glu Ile Gln Asp Pro Asp Gly Tyr Leu
                 165                 170                 175

Asn Thr Met Asp Phe Thr Gly Ile Thr Gly Glu Asn Gly Glu Ser Asp
             180                 185                 190

Leu Phe Glu Phe Gln Tyr Lys Glu Ile Pro Lys Asn Asn Thr Tyr Gly
             195                 200                 205

Ala Glu Val Tyr Leu Thr Leu Lys Asn Asp Lys Thr Leu Asp Tyr Glu
             210                 215                 220

Ser Lys Thr Leu Tyr Ile Phe His Val Glu Ala Lys Asp Gly Ala Gly
225                 230                 235                 240

His Pro Thr Ser Pro Val Ser Ser Val Pro Ile Ile Val Gln Val Asn
                 245                 250                 255

Asp Gln Pro Asp Glu Asn Pro Val Trp Asp Ser Ser Phe Arg Ser Ala
             260                 265                 270

Ile Ser Ile Val Glu Glu Ser Glu Thr Thr Ile Thr Val Ser Ala Lys
             275                 280                 285

Asp Gly Asp Tyr Gly Ile Asn Asn Lys Ile Asn Tyr Lys Ile Glu Phe
             290                 295                 300

Thr Asn Leu Asn Met Ser Pro Ser Ser Asp Asp Ser Asp Leu Ile Thr
305                 310                 315                 320

Ile Asp Pro Glu Thr Gly Val Ile Thr Ile Asn Lys Ile Asp Arg Glu
                 325                 330                 335

Lys Gly Tyr Lys Asp Asp Gln Val Ile Phe Asp Val Thr Ala Phe Glu
             340                 345                 350

Val Pro Asp Pro Ser Ala Lys Ile Thr Asp Gln Val Thr Leu Ile Ile
             355                 360                 365

Gln Asp Ile Asp Asp Asn Ile Pro Glu Ile Thr Thr Lys Asp Gly Ser
370                 375                 380

Lys Pro Leu Gln Ile Gln Val Pro Glu Asn Thr Ala Asp Leu Gly Glu
385                 390                 395                 400

Leu Asp Ile Thr Val Ser Asp Ile Asp Thr Gly Glu Asn Ala Leu Tyr
                 405                 410                 415

Thr Ala Glu Leu Lys Pro Ile Gly Asp Val Asp His Thr Thr Ala Phe
             420                 425                 430

Ser Ile Val Pro Gly Arg Gly Tyr Glu Thr Thr Thr Leu Ile Leu Thr
             435                 440                 445
```

-continued

Val Thr Asp Ser Thr Lys Leu Asp Tyr Glu Asp Ile Glu Trp Arg Glu
450                 455                 460

Ile Gln Leu Lys Leu Glu Thr Thr Gly Thr Lys Asn Pro Ser Gln Thr
465                 470                 475                 480

Asp Thr Leu Asn Ile Thr Ile Thr Leu Gln Asp Leu Asn Asp Glu Ser
            485                 490                 495

Pro Ile Phe Glu Pro Thr Glu Ala Glu Val Asn Ile Lys Glu Thr Val
        500                 505                 510

Thr Lys Gly Ile Thr Ile Tyr Asn Ile Ile Ala Thr Asp Ala Asp Ala
            515                 520                 525

Val Asp Ala Lys Leu Lys His Thr Ile Ser Ser Lys Ser Ala Ala Thr
530                 535                 540

Ile Leu Thr Ile Glu Glu Phe Gly Gly Asn Val Thr Thr Ile Ala Asp
545                 550                 555                 560

Ser Ala Phe Asp Phe Glu Lys Gln Glu Gln Leu Ile Val Gln Ile Gln
                565                 570                 575

Ala Glu Asp Ser Ala Ala Pro Thr Pro His Thr Lys Leu Phe Gln Leu
            580                 585                 590

Thr Ile Asn Val Leu Asp Val Asn Asp Glu Lys Pro Thr Leu Lys Val
        595                 600                 605

Gly Ser Thr Ile Lys Val Asn Glu Asn Gln Glu Asp Gly Ala Ser Leu
        610                 615                 620

Glu Ala Asp Ile Ser Ala Thr Asp Pro Asp Thr Ala Glu Leu Glu
625                 630                 635                 640

Phe Ser Ile Asp Trp Thr Lys Ser Tyr Ala Thr Lys Lys Ser Gln Arg
                645                 650                 655

Ile Lys Asp Glu Val Phe Ala Asp Tyr Asn Cys Ile Lys Val Glu Thr
            660                 665                 670

Glu Leu Val Glu Asn Gly Lys Arg Asn Gln Val Lys Ala Lys Leu Thr
        675                 680                 685

Ile Ile Glu Thr Gln Arg Asn Asn Thr Pro Asp Tyr Glu Thr Phe Asp
690                 695                 700

Asn Leu Tyr Ile Ala Leu Ile Val Thr Asp Asn Asn Thr Glu Val Ser
705                 710                 715                 720

Gly Gln Glu Ser Asp Ser Ala Thr Val Val Ile Ser Ile Gly Asp Leu
                725                 730                 735

Asn Asp Asn Ala Pro Lys Phe Ala Asp Asp Thr Ala Thr Ala Thr Arg
            740                 745                 750

Arg Val Pro Glu Lys Ala Val Asp Gly Thr Leu Ile Thr Thr Val Val
        755                 760                 765

Ala Thr Asp Asp Asp Leu Gly Thr Lys Leu Asn Tyr Ser Ile Glu Arg
        770                 775                 780

Ala Asp Lys Asp Thr Pro Leu Trp Val Ser Ile Asp Glu Thr Ser Gly
785                 790                 795                 800

Ala Ile Ser Val His Leu Glu Lys Asn Glu Ile Asp Cys Asp Asp
                805                 810                 815

Pro Pro Arg Asp Asp Leu Lys Tyr Ile Val Thr Val Thr Asp Gly Lys
            820                 825                 830

Tyr Asn Asp Thr Ala Thr Ile Thr Ile Gly Ile Asp Asp Glu Asn Glu
            835                 840                 845

Asn Lys Pro Thr Val Gln Asn Val Thr Val Thr Thr Leu Gln Glu Gln
        850                 855                 860

Asp Glu Gln Ser Gln Asp Asp Ser Ser Pro Asn Gly Lys Ile Val Ala

-continued

```
865                 870                 875                 880
Glu Ile Lys Tyr Thr Asp Ile Asp Arg Asp Ala Glu Tyr Lys Lys Val
                885                 890                 895
Ser Cys Gly Phe Ala Ser Ser Thr Ser Asp Val Thr Asn Arg Phe
                900                 905                 910
Asp Ile Val Asn Asn Thr Ile Lys Val Lys Leu Glu Asp Gly Tyr Asp
                915                 920                 925
Leu Asp Arg Glu Lys Asn Pro Thr Phe Thr Glu Leu Asn Cys Val
930                 935                 940
Asp Asn Pro Thr Lys Gln Gly Ser Gly Ile Ser Asn Ala Ala Glu Ser
945                 950                 955                 960
Ile Pro Lys Val Phe Ile Ala Leu Gln Asp Ile Asn Asp Lys Arg Pro
                965                 970                 975
Ile Ile Thr Asn Gln Asp Ile Lys Gly Ile Asp Glu Ser Thr Ser Gly
                980                 985                 990
Ser Ile Gly Thr Gln Leu Ile Gly Lys Asp Glu Asp Glu Ser Lys Asn
                995                 1000                1005
Gly Gln Ile His Tyr Asn Gly Ile Thr Ala Ile Lys Arg Tyr Ile
        1010                1015                1020
Asn Glu Asn Asp Ala Ser Pro Val Asp Pro Pro Gln Asp Leu
        1025                1030                1035
Ile Lys Val Glu Asp Ala Gly Asp Asp Lys Asn Ala Asn Leu Thr
        1040                1045                1050
Ile Thr Ala Glu Asn Leu Glu Asn Tyr Tyr Gly Tyr Leu Lys Leu
        1055                1060                1065
Asn Ile Ser Phe Thr Asp Lys Gly Asp Ser Pro Leu Val Asn Glu
        1070                1075                1080
Glu Val Val Thr Leu Glu Val Ala Lys Tyr Asn Phe Lys Glu Pro
        1085                1090                1095
Thr Phe Thr Phe Pro Thr Gln Gly Lys Ser Ile Phe Leu Gln Lys
        1100                1105                1110
Ser Gln Glu Pro Asn Ser Arg Leu Tyr Leu Phe Asn Gly Glu Ala
        1115                1120                1125
Leu Glu Asp Phe Val Val Asp Gly Gln Lys Gly Lys Phe Ser
        1130                1135                1140
Phe Asn Tyr Lys Val Leu Asp Ala Ser Val Thr Gly Ile Phe Asn
        1145                1150                1155
Met Lys Asn Asn Gln Leu Gln Ile Ile Asn Ala Ala Tyr Asp Thr
        1160                1165                1170
Glu Met Ile Tyr Lys Leu Thr Val Glu Ala Ser Ile Lys Glu Gln
        1175                1180                1185
Thr Gln Ile Asn Gly Lys Pro Thr Phe Ala Arg Cys Glu Phe Asn
        1190                1195                1200
Val Gly Phe Phe Asp Lys Asp Asn Thr Asp Pro Ile Phe Lys Asn
        1205                1210                1215
Lys His Glu Asp Thr His Glu Met Ala Glu Glu Asp Asp Thr Leu
        1220                1225                1230
Phe Tyr Val Leu Ile Glu Asn Ala Thr Tyr Ala Lys Glu Asp Val
        1235                1240                1245
Pro Asp Asp Leu Ser Thr Phe Tyr Leu Leu Ala Glu Gly Glu Arg
        1250                1255                1260
Asp Ile Phe Asp Val Asp Lys Phe Thr Gly Lys Val Thr Leu Asn
        1265                1270                1275
```

-continued

```
Lys Pro Leu Asp Tyr Glu Thr Lys Lys Ser His Ser Leu Thr Ile
    1280                1285                1290

Gln Ser Ser Asn Ser Asp Lys Leu Lys Leu Asn Ala Ser Glu Glu
    1295                1300                1305

Thr Lys Leu His Leu Thr Ile Ile Val Thr Asp Ile Asn Asp His
    1310                1315                1320

Ala Pro Val Met Asp Ser Asp Ser Tyr Ile Thr Val Leu Pro Leu
    1325                1330                1335

Val Asp Ala Val Ser Thr Ala Lys Leu Val Thr Ile His Ala Thr
    1340                1345                1350

Asp Pro Asp Asp Thr Ser Glu Val Gln Tyr Gln Ile Glu Ser Cys
    1355                1360                1365

Ile Gly Ser Gly Asp Leu Leu Gln Lys Leu Cys Gly Asn Asn Pro
    1370                1375                1380

Phe Glu Ile Asn Lys Ile Ser Gly Glu Ile Ser Ala Gln Ile Gln
    1385                1390                1395

Ser Ala Asn Leu Ser Lys Trp Asp Gly His Phe Asn Leu Thr Val
    1400                1405                1410

Thr Ala Ala Asp Glu Ala Gly Phe Asp Asp Lys Asn His Thr Asp
    1415                1420                1425

Glu Ala Val Val Thr Leu Tyr Leu Val Thr Lys Leu His Leu Val
    1430                1435                1440

Ala Phe Asp Phe Glu Asn Ser Leu Glu Gln Val Gln Asn Lys Ser
    1445                1450                1455

Asn Glu Ile Lys Thr Ile Leu Asp Glu Gln Phe Ala Glu Thr Ser
    1460                1465                1470

Asp Gly Gly Thr Pro Tyr Val Ala Thr Val Gln Gly Ala Asn Ala
    1475                1480                1485

Lys Ser Asp Glu Ile Thr Thr Ala Thr Val Tyr Phe Leu Asn Leu
    1490                1495                1500

Lys Gln Gln Lys Pro Val Asn Lys Asp Asn Ile Tyr Ser Tyr Cys
    1505                1510                1515

Thr Asn Thr Gln Tyr Phe Gly Ser Met Arg Ser Ala Phe Leu Ala
    1520                1525                1530

Glu Gly Leu Ser Leu Met Ser Phe Asp Gly Thr Ser Asn Glu Thr
    1535                1540                1545

Glu Asp Met Glu Glu Ile Leu Thr Ala Trp Leu Ile Gly Val Ser
    1550                1555                1560

Val Val Leu Gly Ala Leu Cys Ile Ile Leu Ser Ile Ala Phe Ile
    1565                1570                1575

Leu Lys Thr Arg Ser Leu Asn Gln Arg Ile Asp Lys Leu Ser Ser
    1580                1585                1590

Thr Lys Phe Gly Ser Gln Glu Ser Gly Leu Asn Arg Thr Gly Val
    1595                1600                1605

Ala Ala Pro Thr Thr Asn Lys His Ala Val Glu Gly Ser Asn Pro
    1610                1615                1620

Val Tyr Asn Asn Glu Val Asp Thr Asn Glu Val Asp Arg Arg Val
    1625                1630                1635

Ser Val Ala Ser Gly Gly Ser Glu Leu Ile Gly Ile Glu Asp Asp
    1640                1645                1650

Asp Lys Phe Asn Tyr Asn Ser Tyr Pro Thr Lys Asp Glu Glu Asn
    1655                1660                1665
```

Ala Glu Glu Glu Asn
    1670

<210> SEQ ID NO 3
<211> LENGTH: 465
<212> TYPE: DNA
<213> ORGANISM: Alphitobius diaperinus

<400> SEQUENCE: 3
accgaaatga tatacaagct aacggttgaa gcaagtataa aggaacaaac gcaaataaat      60
ggtaaaccca cttttgcaag gtgcgaattt aacgtcgggt tcttcgataa agataacacc     120
gatccaatct tcaaaaataa acacgaagat actcatgaaa tggctgagga agatgataca     180
ttgttttatg tactgataga aaatgcaacc tacgccaaag aagatgttcc tgacgattta     240
agcacatttt atttgttagc agaaggagag agggatattt tcgatgttga caaattcact     300
ggaaaagtca ctttgaataa accattggat tatgaaacca aaaaaagcca cagcttgacg     360
atacagtcat ctaattctga taagttgaaa ctaaatgcca gtgaagagac gaaattacat     420
ctaaccatca ttgtgacaga tattaacgac catgctcctg taatg                    465

<210> SEQ ID NO 4
<211> LENGTH: 155
<212> TYPE: PRT
<213> ORGANISM: Alphitobius diaperinus

<400> SEQUENCE: 4

Thr Glu Met Ile Tyr Lys Leu Thr Val Glu Ala Ser Ile Lys Glu Gln
1               5                   10                  15

Thr Gln Ile Asn Gly Lys Pro Thr Phe Ala Arg Cys Glu Phe Asn Val
            20                  25                  30

Gly Phe Phe Asp Lys Asp Asn Thr Asp Pro Ile Phe Lys Asn Lys His
        35                  40                  45

Glu Asp Thr His Glu Met Ala Glu Asp Asp Thr Leu Phe Tyr Val
    50                  55                  60

Leu Ile Glu Asn Ala Thr Tyr Ala Lys Glu Asp Val Pro Asp Asp Leu
65                  70                  75                  80

Ser Thr Phe Tyr Leu Leu Ala Glu Gly Glu Arg Asp Ile Phe Asp Val
                85                  90                  95

Asp Lys Phe Thr Gly Lys Val Thr Leu Asn Lys Pro Leu Asp Tyr Glu
            100                 105                 110

Thr Lys Lys Ser His Ser Leu Thr Ile Gln Ser Ser Asn Ser Asp Lys
        115                 120                 125

Leu Lys Leu Asn Ala Ser Glu Glu Thr Lys Leu His Leu Thr Ile Ile
    130                 135                 140

Val Thr Asp Ile Asn Asp His Ala Pro Val Met
145                 150                 155

<210> SEQ ID NO 5
<211> LENGTH: 687
<212> TYPE: DNA
<213> ORGANISM: Alphitobius diaperinus

<400> SEQUENCE: 5
gattccgatt cttacattac agtattacca ttagtggacg cagtctcgac tgcaaaattg      60
gtgacaatac acgctacaga tccagatgac acaagcgaag tgcagtatca gattgaatcc     120
tgcattggct ctggagatct tttacaaaag ctatgtggca taatcccttt gaaataaat     180

```
aaaattagtg gtgaaatttc cgctcagatt caatcagcga atcttagtaa atgggatggt    240
catttcaatt taacagttac agcggccgat gaggctggtt tcgatgacaa aaatcacaca    300
gacgaagcag ttgtgacact atatctcgtc acaaaactac atcttgtagc atttgatttt    360 gaaatagct tagaacaagt tcaaaataaa agtaacgaaa tcaaaacaat cctcgatgaa     420
caatttgctg aaacttctga tggtggaaca ccatacgtag ccactgtaca aggcgcaaac    480
gctaaatccg atgaaattac aacagcaacc gtatattttc tgaatcttaa acaacagaaa    540
ccagtaaata aagataatat atacagttat tgtactaaca ctcagtattt cggaagtatg    600
agatcagctt tcttagcaga gggtttatca ttaatgagtt ttgacggaac ctctaacgaa    660
actgaagata tggaggagat tttaacg                                        687
```

```
<210> SEQ ID NO 6
<211> LENGTH: 229
<212> TYPE: PRT
<213> ORGANISM: Alphitobius diaperinus

<400> SEQUENCE: 6

Asp Ser Asp Ser Tyr Ile Thr Val Leu Pro Leu Val Asp Ala Val Ser
1               5                   10                  15

Thr Ala Lys Leu Val Thr Ile His Ala Thr Asp Pro Asp Asp Thr Ser
            20                  25                  30

Glu Val Gln Tyr Gln Ile Glu Ser Cys Ile Gly Ser Gly Asp Leu Leu
        35                  40                  45

Gln Lys Leu Cys Gly Asn Asn Pro Phe Glu Ile Asn Lys Ile Ser Gly
    50                  55                  60

Glu Ile Ser Ala Gln Ile Gln Ser Ala Asn Leu Ser Lys Trp Asp Gly
65                  70                  75                  80

His Phe Asn Leu Thr Val Thr Ala Ala Asp Glu Ala Gly Phe Asp Asp
                85                  90                  95

Lys Asn His Thr Asp Glu Ala Val Val Thr Leu Tyr Leu Val Thr Lys
            100                 105                 110

Leu His Leu Val Ala Phe Asp Phe Glu Asn Ser Leu Glu Gln Val Gln
        115                 120                 125

Asn Lys Ser Asn Glu Ile Lys Thr Ile Leu Asp Glu Gln Phe Ala Glu
    130                 135                 140

Thr Ser Asp Gly Gly Thr Pro Tyr Val Ala Thr Val Gln Gly Ala Asn
145                 150                 155                 160

Ala Lys Ser Asp Glu Ile Thr Thr Ala Thr Val Tyr Phe Leu Asn Leu
                165                 170                 175

Lys Gln Gln Lys Pro Val Asn Lys Asp Asn Ile Tyr Ser Tyr Cys Thr
            180                 185                 190

Asn Thr Gln Tyr Phe Gly Ser Met Arg Ser Ala Phe Leu Ala Glu Gly
        195                 200                 205

Leu Ser Leu Met Ser Phe Asp Gly Thr Ser Asn Glu Thr Glu Asp Met
    210                 215                 220

Glu Glu Ile Leu Thr
225
```

```
<210> SEQ ID NO 7
<211> LENGTH: 20
<212> TYPE: DNA
<213> ORGANISM: Artificial Sequence
<220> FEATURE:
<223> OTHER INFORMATION: Primer sequence AdCad1-Sense1
```

<400> SEQUENCE: 7
tatcagggaa tacctacccg                                              20

<210> SEQ ID NO 8
<211> LENGTH: 21
<212> TYPE: DNA
<213> ORGANISM: Artificial Sequence
<220> FEATURE:
<223> OTHER INFORMATION: Primer sequence AdCad1-Antisense1

<400> SEQUENCE: 8
cagtgtcaga taaacctcag c                                            21

<210> SEQ ID NO 9
<211> LENGTH: 40
<212> TYPE: DNA
<213> ORGANISM: Artificial Sequence
<220> FEATURE:
<223> OTHER INFORMATION: Primer sequence AdCad1-T7-Sense1

<400> SEQUENCE: 9
taatacgact cactataggg tatcagggaa tacctacccg                        40

<210> SEQ ID NO 10
<211> LENGTH: 40
<212> TYPE: DNA
<213> ORGANISM: Artificial Sequence
<220> FEATURE:
<223> OTHER INFORMATION: Primer sequence AdCad1-T7-Antisense1

<400> SEQUENCE: 10
taatacgact cactataggg gacaaagttg ggctctcatc                        40

<210> SEQ ID NO 11
<211> LENGTH: 21
<212> TYPE: DNA
<213> ORGANISM: Artificial Sequence
<220> FEATURE:
<223> OTHER INFORMATION: Primer sequence AdCad1-Sense2

<400> SEQUENCE: 11
cagcgaatct tagtaaatgg g                                            21

<210> SEQ ID NO 12
<211> LENGTH: 21
<212> TYPE: DNA
<213> ORGANISM: Artificial Sequence
<220> FEATURE:
<223> OTHER INFORMATION: Primer sequence AdCad1-Antisense2

<400> SEQUENCE: 12
taaaccctct gctaagaaag c                                            21

<210> SEQ ID NO 13
<211> LENGTH: 41
<212> TYPE: DNA
<213> ORGANISM: Artificial Sequence
<220> FEATURE:
<223> OTHER INFORMATION: Primer sequence AdCad1-T7-Sense2

<400> SEQUENCE: 13
taatacgact cactataggg cagcgaatct tagtaaatgg g                      41

<210> SEQ ID NO 14
<211> LENGTH: 39

```
<212> TYPE: DNA
<213> ORGANISM: Artificial Sequence
<220> FEATURE:
<223> OTHER INFORMATION: Primer sequence AdCad1-T7-Antisense2

<400> SEQUENCE: 14
taatacgact cactataggg gccttgtaca gtggctacg                        39

<210> SEQ ID NO 15
<211> LENGTH: 21
<212> TYPE: DNA
<213> ORGANISM: Artificial Sequence
<220> FEATURE:
<223> OTHER INFORMATION: Primer sequence RT-qPCR Primer

<400> SEQUENCE: 15
ggcagctcct accactaaca a                                          21

<210> SEQ ID NO 16
<211> LENGTH: 21
<212> TYPE: DNA
<213> ORGANISM: Artificial Sequence
<220> FEATURE:
<223> OTHER INFORMATION: Primer sequence RT-qPCR Primer

<400> SEQUENCE: 16
atgccaatca actcggaacc t                                          21

<210> SEQ ID NO 17
<211> LENGTH: 8
<212> TYPE: PRT
<213> ORGANISM: Artificial Sequence
<220> FEATURE:
<223> OTHER INFORMATION: MsBtR1-CR12 cadherin region binding motif

<400> SEQUENCE: 17

Gly Val Leu Thr Leu Asn Ile Gln
1               5

<210> SEQ ID NO 18
<211> LENGTH: 8
<212> TYPE: PRT
<213> ORGANISM: Artificial Sequence
<220> FEATURE:
<223> OTHER INFORMATION: HvCad1-CR11 cadherin region binding motif

<400> SEQUENCE: 18

Gly Val Leu Thr Leu Asn Phe Gln
1               5

<210> SEQ ID NO 19
<211> LENGTH: 8
<212> TYPE: PRT
<213> ORGANISM: Artificial Sequence
<220> FEATURE:
<223> OTHER INFORMATION: TcCAD1-CR12 cadherin region binding motif

<400> SEQUENCE: 19

Gly Val Ile Lys Tyr Asn Phe Lys
1               5

<210> SEQ ID NO 20
<211> LENGTH: 8
<212> TYPE: PRT
<213> ORGANISM: Artificial Sequence
<220> FEATURE:
<223> OTHER INFORMATION: TcSSS cadherin -continued

<400> SEQUENCE: 20

Gly Ser Ala Thr Val Glu Leu Lys
1               5

<210> SEQ ID NO 21
<211> LENGTH: 8
<212> TYPE: PRT
<213> ORGANISM: Artificial Sequence
<220> FEATURE:
<223> OTHER INFORMATION: TmCad1-CR12 cadherin region binding motif

<400> SEQUENCE: 21

Gly Asp Ile Thr Ile Asn Phe Glu
1               5

<210> SEQ ID NO 22
<211> LENGTH: 8
<212> TYPE: PRT
<213> ORGANISM: Artificial Sequence
<220> FEATURE:
<223> OTHER INFORMATION: AdCad1-CR9 cadherin region binding motif

<400> SEQUENCE: 22

Gly Lys Val Thr Leu Asn Lys Pro
1               5

<210> SEQ ID NO 23
<211> LENGTH: 8
<212> TYPE: PRT
<213> ORGANISM: Artificial Sequence
<220> FEATURE:
<223> OTHER INFORMATION: AdCad1-MPED cadherin region binding motif

<400> SEQUENCE: 23

Gly Glu Ile Ser Ala Gln Ile Gln
1               5

<210> SEQ ID NO 24
<211> LENGTH: 28
<212> TYPE: DNA
<213> ORGANISM: Artificial Sequence
<220> FEATURE:
<223> OTHER INFORMATION: Primer sequence Ad1 Forward

<400> SEQUENCE: 24
aaatccgatg aaattacaac agcaaccg                                      28

<210> SEQ ID NO 25
<211> LENGTH: 32
<212> TYPE: DNA
<213> ORGANISM: Artificial Sequence
<220> FEATURE:
<223> OTHER INFORMATION: Primer sequence Ad2 Forward

<400> SEQUENCE: 25
gaatcttaaa caacagaaac cagtaaataa ag                                 32

<210> SEQ ID NO 26
<211> LENGTH: 32
<212> TYPE: DNA
<213> ORGANISM: Artificial Sequence
<220> FEATURE:
<223> OTHER INFORMATION: Primer sequence Ad3 Reverse

<400> SEQUENCE: 26

```
ctttatttac tggtttctgt tgtttaagat tc                              32

<210> SEQ ID NO 27
<211> LENGTH: 28
<212> TYPE: DNA
<213> ORGANISM: Artificial Sequence
<220> FEATURE:
<223> OTHER INFORMATION: Primer sequence Ad4 Reverse

<400> SEQUENCE: 27
ccctctgcta agaaagctga tctcatac                                   28

<210> SEQ ID NO 28
<211> LENGTH: 28
<212> TYPE: DNA
<213> ORGANISM: Artificial Sequence
<220> FEATURE:
<223> OTHER INFORMATION: Primer sequence Ad5 Forward

<400> SEQUENCE: 28
gggtctacga ttaaggtgaa tgaaaacc                                   28

<210> SEQ ID NO 29
<211> LENGTH: 29
<212> TYPE: DNA
<213> ORGANISM: Artificial Sequence
<220> FEATURE:
<223> OTHER INFORMATION: Primer sequence Ad6 Forward

<400> SEQUENCE: 29
ggtgcctcac tcgaagcgga tatttctgc                                  29

<210> SEQ ID NO 30
<211> LENGTH: 25
<212> TYPE: DNA
<213> ORGANISM: Artificial Sequence
<220> FEATURE:
<223> OTHER INFORMATION: Primer sequence Ad7 Reverse

<400> SEQUENCE: 30
cggaatcact ttcttgtccg gagac                                      25

<210> SEQ ID NO 31
<211> LENGTH: 28
<212> TYPE: DNA
<213> ORGANISM: Artificial Sequence
<220> FEATURE:
<223> OTHER INFORMATION: Primer sequence Ad8 Reverse

<400> SEQUENCE: 31
cttggcttta acttgatttc gttttccg                                   28

<210> SEQ ID NO 32
<211> LENGTH: 30
<212> TYPE: DNA
<213> ORGANISM: Artificial Sequence
<220> FEATURE:
<223> OTHER INFORMATION: Primer sequence Ad9 Forward

<400> SEQUENCE: 32
cgcacatatg accgaaatga tatacaagct                                 30

<210> SEQ ID NO 33
<211> LENGTH: 32
<212> TYPE: DNA
<213> ORGANISM: Artificial Sequence
```

<220> FEATURE:
<223> OTHER INFORMATION: Primer sequence Ad10 Reverse

<400> SEQUENCE: 33
aatcctcgag cattacagga gcatggtcgt ta                                32

<210> SEQ ID NO 34
<211> LENGTH: 28
<212> TYPE: DNA
<213> ORGANISM: Artificial Sequence
<220> FEATURE:
<223> OTHER INFORMATION: Primer sequence Ad11 Forward

<400> SEQUENCE: 34
tcctcatatg gattccgatt cttacatt                                    28

<210> SEQ ID NO 35
<211> LENGTH: 32
<212> TYPE: DNA
<213> ORGANISM: Artificial Sequence
<220> FEATURE:
<223> OTHER INFORMATION: Primer sequence Ad12 Reverse

<400> SEQUENCE: 35
taagctcgag cgttaaaatc tcctccatat ct                               32

<210> SEQ ID NO 36
<211> LENGTH: 29
<212> TYPE: DNA
<213> ORGANISM: Artificial Sequence
<220> FEATURE:
<223> OTHER INFORMATION: Primer sequence Ad13 Forward

<400> SEQUENCE: 36
gatcagtagg gtaatacaag atgaagctc                                   29

<210> SEQ ID NO 37
<211> LENGTH: 22
<212> TYPE: DNA
<213> ORGANISM: Artificial Sequence
<220> FEATURE:
<223> OTHER INFORMATION: Primer sequence Ad14 Forward

<400> SEQUENCE: 37
gcaactgatg cggacgcagt gg                                          22

<210> SEQ ID NO 38
<211> LENGTH: 24
<212> TYPE: DNA
<213> ORGANISM: Artificial Sequence
<220> FEATURE:
<223> OTHER INFORMATION: Primer sequence Ad15 Forward

<400> SEQUENCE: 38
aaagtcaaga gcctaacagc agac                                        24

<210> SEQ ID NO 39
<211> LENGTH: 32
<212> TYPE: DNA
<213> ORGANISM: Artificial Sequence
<220> FEATURE:
<223> OTHER INFORMATION: Primer sequence Ad16 Reverse

<400> SEQUENCE: 39
aaataacatt aaacttaatt ctcttcttct gc                               32

<210> SEQ ID NO 40
<211> LENGTH: 24
<212> TYPE: DNA
<213> ORGANISM: Artificial Sequence
<220> FEATURE:
<223> OTHER INFORMATION: Primer sequence Ad17 Reverse

<400> SEQUENCE: 40
gtagtggatg atggacaaaa gggg                                        24

<210> SEQ ID NO 41
<211> LENGTH: 28
<212> TYPE: DNA
<213> ORGANISM: Artificial Sequence
<220> FEATURE:
<223> OTHER INFORMATION: Primer sequence Ad18 Reverse

<400> SEQUENCE: 41
gggtccacga ttaaggtgaa tgaaaacc                                    28

<210> SEQ ID NO 42
<211> LENGTH: 20
<212> TYPE: DNA
<213> ORGANISM: Artificial Sequence
<220> FEATURE:
<223> OTHER INFORMATION: Primer sequence Ad19 Forward

<400> SEQUENCE: 42
tatcagggaa tacctacccg                                             20

<210> SEQ ID NO 43
<211> LENGTH: 21
<212> TYPE: DNA
<213> ORGANISM: Artificial Sequence
<220> FEATURE:
<223> OTHER INFORMATION: Primer sequence Ad20 Reverse

<400> SEQUENCE: 43
cagtgtcaga taaacctcag c                                           21

<210> SEQ ID NO 44
<211> LENGTH: 40
<212> TYPE: DNA
<213> ORGANISM: Artificial Sequence
<220> FEATURE:
<223> OTHER INFORMATION: Primer sequence Ad21 Forward

<400> SEQUENCE: 44
taatacgact cactataggg tatcagggaa tacctacccg                       40

<210> SEQ ID NO 45
<211> LENGTH: 40
<212> TYPE: DNA
<213> ORGANISM: Artificial Sequence
<220> FEATURE:
<223> OTHER INFORMATION: Primer sequence Ad22 Reverse

<400> SEQUENCE: 45
taatacgact cactataggg gacaaagttg ggctctcatc                       40

<210> SEQ ID NO 46
<211> LENGTH: 21
<212> TYPE: DNA
<213> ORGANISM: Artificial Sequence
<220> FEATURE:
<223> OTHER INFORMATION: Primer sequence Ad23 Forward

```
<400> SEQUENCE: 46
cagcgaatct tagtaaatgg g                                              21

<210> SEQ ID NO 47
<211> LENGTH: 21
<212> TYPE: DNA
<213> ORGANISM: Artificial Sequence
<220> FEATURE:
<223> OTHER INFORMATION: Primer sequence Ad24 Reverse

<400> SEQUENCE: 47
gctttcttag cagagggttt a                                              21

<210> SEQ ID NO 48
<211> LENGTH: 41
<212> TYPE: DNA
<213> ORGANISM: Artificial Sequence
<220> FEATURE:
<223> OTHER INFORMATION: Primer sequence Ad25 Forward

<400> SEQUENCE: 48
taatacgact cactataggg cagcgaatct tagtaaatgg g                        41

<210> SEQ ID NO 49
<211> LENGTH: 39
<212> TYPE: DNA
<213> ORGANISM: Artificial Sequence
<220> FEATURE:
<223> OTHER INFORMATION: Primer sequence Ad26 Reverse

<400> SEQUENCE: 49
taatacgact cactataggg gccttgtaca gtggctacg                           39

<210> SEQ ID NO 50
<211> LENGTH: 21
<212> TYPE: DNA
<213> ORGANISM: Artificial Sequence
<220> FEATURE:
<223> OTHER INFORMATION: Primer sequence AdCad1/qPCR-f Forward

<400> SEQUENCE: 50
ggcagctcct accactaaca a                                              21

<210> SEQ ID NO 51
<211> LENGTH: 21
<212> TYPE: DNA
<213> ORGANISM: Artificial Sequence
<220> FEATURE:
<223> OTHER INFORMATION: Primer sequence AdCad1/qPCR-r Reverse

<400> SEQUENCE: 51
atgccaatca actcggaacc t                                              21

<210> SEQ ID NO 52
<211> LENGTH: 20
<212> TYPE: DNA
<213> ORGANISM: Artificial Sequence
<220> FEATURE:
<223> OTHER INFORMATION: Primer sequence AdRPS6/qPCR-f Forward

<400> SEQUENCE: 52
cccaaaattc agcgtctcat                                                20

<210> SEQ ID NO 53
```

```
<211> LENGTH: 20
<212> TYPE: DNA
<213> ORGANISM: Artificial Sequence
<220> FEATURE:
<223> OTHER INFORMATION: Primer sequence AdRPS6/qPCR-r Reverse

<400> SEQUENCE: 53
tcttcaaggc caacctatgg                                               20

<210> SEQ ID NO 54
<211> LENGTH: 8
<212> TYPE: PRT
<213> ORGANISM: Artificial Sequence
<220> FEATURE:
<223> OTHER INFORMATION: DvCad1-CR8-10 peptide predicted binding site

<400> SEQUENCE: 54

Ser Ser Leu Asn Val Thr Val Asn
1               5
```

CADHERIN FRAGMENTS FOR MANAGING INSECT RESISTANCE TO CRY PROTEINS

CROSS-REFERENCE TO RELATED APPLICATIONS

This application is a divisional of U.S. patent application Ser. No. 14/072,619, filed Nov. 5, 2013, which claims priority to U.S. Provisional Application No. 61/722,592, filed on Nov. 5, 2012, each of which is expressly incorporated herein by reference in their entireties.

STATEMENT REGARDING FEDERALLY SPONSORED RESEARCH

This research was supported by U.S. NIFA award number 2010-65105-20590 to M. J. Adang (University of Georgia). The U.S. Government has certain rights in this invention.

SEQUENCE LISTING

The instant application contains a Sequence Listing which has been submitted via EFS-web and is hereby incorporated by reference in its entirety. The ASCII copy, created on Feb. 6, 2017, is named 20170206_981791.46_Sequence_Listing_ST25, and is 36,469 bytes in size.

BACKGROUND

*Bacillus thuringiensis* (Bt) Cry proteins are essential tools in Western corn rootworm (WCRW) management, which have the potential to control other coleopteran pests, including the lesser mealworm (LMW) and white grubs. Cry3Bb is moderately toxic to WCRW, which is expressed in corn hybrids. Cry8Ca is toxic to white grubs, pests of turf.

Cry3Bb and Cry8Ca were identified as being as toxic to LMW, a pest of poultry production and a reservoir for *Salmonella*.

BtBoosters (BtB), which synergize or enhance activity of Cry proteins, were known. Below is the first report of BtBs being used to overcome insects that are resistant to a Cry protein.

SUMMARY

The subject disclosure relates in part to a combination of a cadherin peptide and a Cry protein that will overcome resistance in insects to the Cry protein alone. Cadherin peptides that enhance Cry proteins are called BtBoosters.

The subject disclosure relates in part to the use of a cadherin fragment to suppress Cry resistance in insects. Disclosed herein is a showing for the first time that cadherin fragments may serve as a management tool for insect resistance.

Using RNAi knock-down, we established that beetles with cadherin expression inhibited by RNAi are not killed by beetle-active Cry3Bb toxin. This is an insecticidal toxin in Bt corn used for rootworm control. Feeding the Bt-resistant beetle larvae (RNAi inhibition), the Cry3Bb with the cadherin fragment completely overcomes resistance to the Bt Cry toxin.

BRIEF DESCRIPTION OF THE SEQUENCES

Figure 1A:
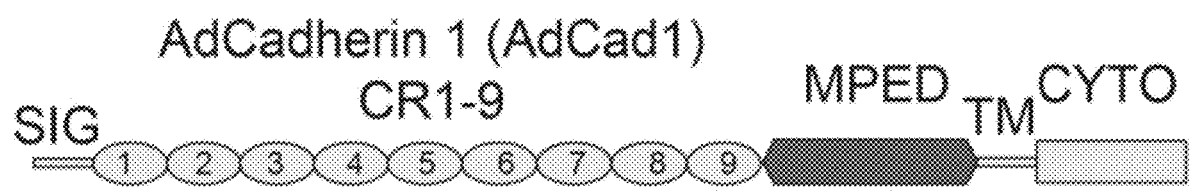
FIG. 1A is an illustration depicting the conserved domain structure of cadherin repeats, MPED, signal peptide, and transmembrane domain of the *A. diaperinus* cadherin 1.
Figure 1B:
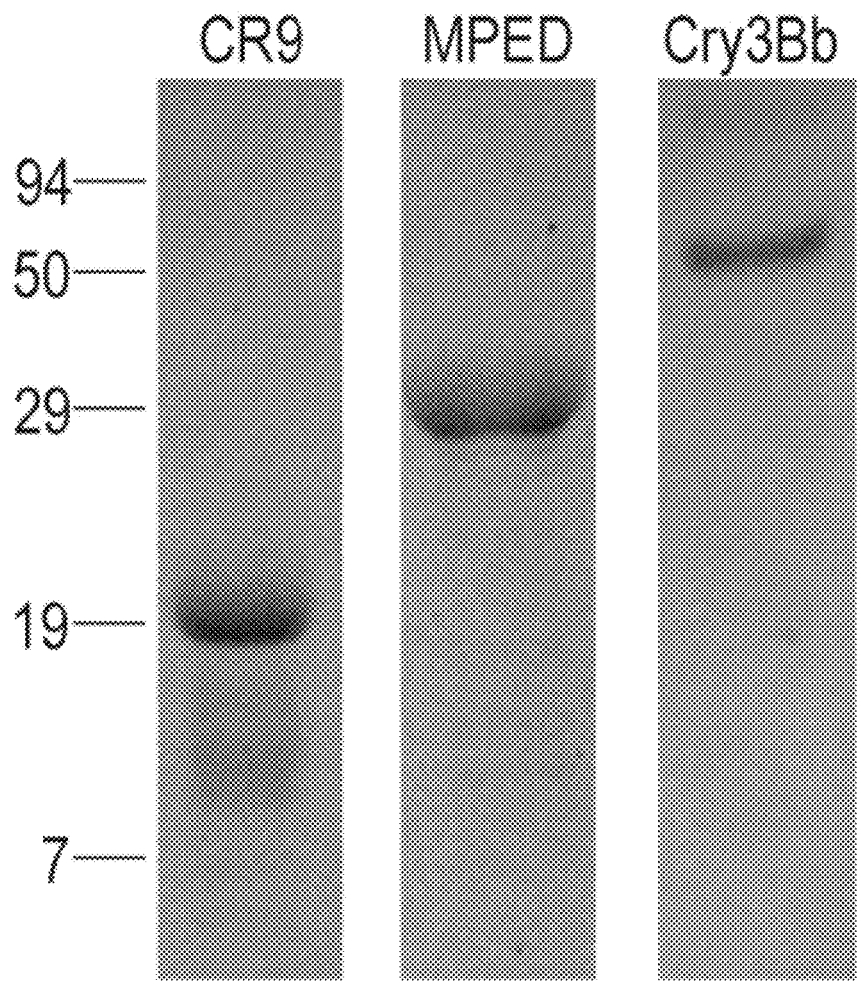
FIG. 1B is a photograph of an SDS-PAGE gel representing *E. coli* expressed and purified AdCad1-CR9, AdCad1-MPED and Cry3Bb on 12% SDS-PAGE with CBB-staining.
Figure 2A:
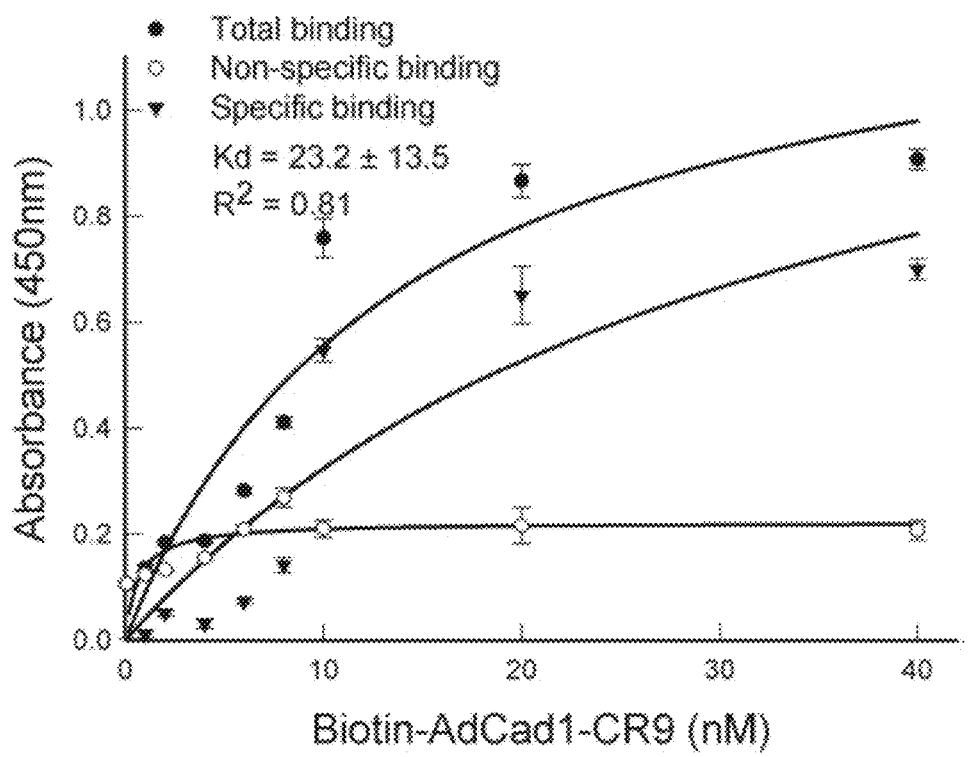
FIGS. 2A-2B are graphs indicating binding affinities of Cry3Bb for AdCad1-CR9 (FIG. 2A) and AdCad1-MPED (FIG. 2B) peptides. Microtiter plates coated with 1.0 µg of trypsinized Cry3Bb per well were incubated with increasing concentrations of biotinylated-AdCad1-CR9 or -AdCad1-MPED alone, or with 1000-fold molar excess of unlabeled homologous peptide to determine specific binding. Each data point is the mean of the results from two experiments done in triplicate. Error bars depict standard deviations. Binding affinities ($K_d$) were calculated based on specifically bound biotinylated peptides using a one-site saturation binding equation.
Figure 2B:
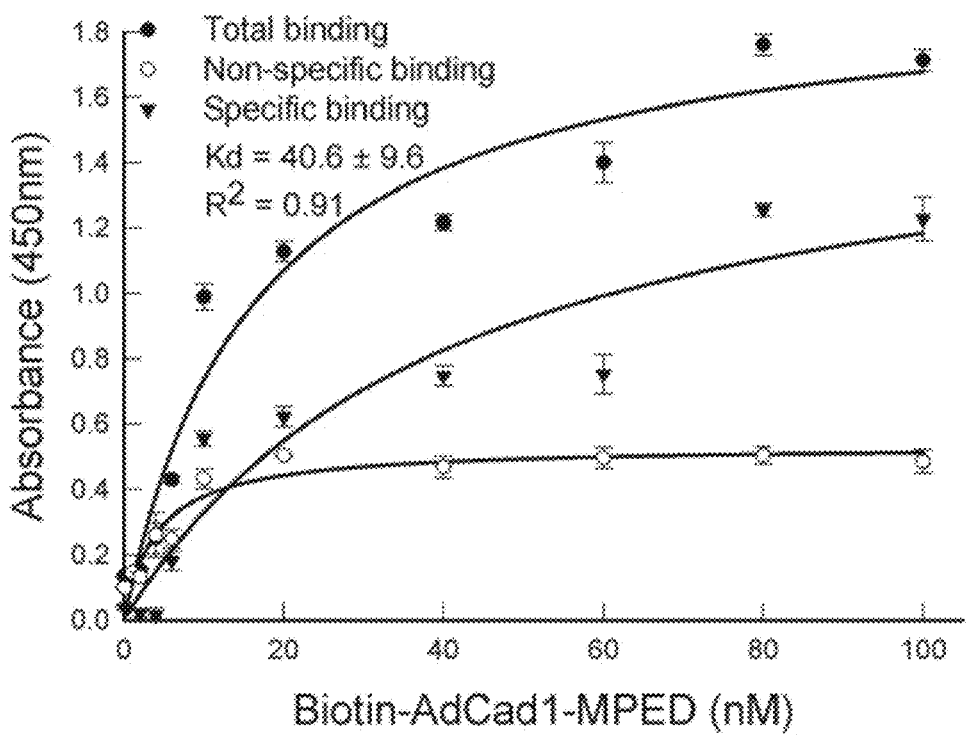

SEQ ID NO: 1 is the AdCad1 nucleotide sequence.
SEQ ID NO: 2 is the AdCad1 amino acid sequence.
SEQ ID NO: 3 is the AdCad1-CR9 nucleotide sequence, which corresponds to nucleic acids 3317-3981 of SEQ ID NO: 1.
SEQ ID NO: 4 is the AdCad1-CR9 amino acid sequence, which corresponds to amino acids 1173-1327 of SEQ ID NO: 2.

SEQ ID NO: 5 is the AdCad1-MPED nucleotide sequence, which corresponds to nucleic acids 3982-4668 of SEQ ID NO: 1.

SEQ ID NO: 6 is the AdCad1-MPED amino acid sequence, which corresponds to amino acids 1328-1556 of SEQ ID NO: 2.

SEQ ID NO: 7 is the nucleotide sequence for the primer designated AdCad1-Sense 1.

SEQ ID NO: 8 is the nucleotide sequence for the primer designated AdCad1-Antisense 1.

SEQ ID NO: 9 is the nucleotide sequence for the primer designated AdCad1-T7-Sense 1.

SEQ ID NO: 10 is the nucleotide sequence for the primer designated AdCad1-T7-Antisense 1.

SEQ ID NO: 11 is the nucleotide sequence for the primer designated AdCad1-Sense2.

SEQ ID NO: 12 is the nucleotide sequence for the primer designated AdCad1-Antisense2.

SEQ ID NO: 13 is the nucleotide sequence for the primer designated AdCad1-T7-Sense2.

SEQ ID NO: 14 is the nucleotide sequence for the primer designated AdCad1-T7-Antisense2.

SEQ ID NO: 15 is the nucleotide sequence for the primer designated RT-qPCR Primer 1.

SEQ ID NO: 16 is the nucleotide sequence for the primer designated RT-qPCR Primer2.

SEQ ID NOS: 17-23 are designated binding regions further described in Table 1.

SEQ ID NOS: 24-41 represent primers Ad1-18, respectively, as described in Table 2.

SEQ ID NOS: 42-53 represent primers Ad19-26 and qPCR primers, as described in Table 3.

SEQ ID NO: 54 is the amino acid sequence for the predicted binding site of DvCad1-CR8-10.

DETAILED DESCRIPTION

*Bacillus thuringiensis* (Bt) Cry proteins are used as components of biopesticides or expressed in transgenic crops to control diverse insect pests worldwide. These Cry toxins bind to receptors on the midgut brush border membrane and kill enterocytes culminating in larval mortality. Cadherin proteins have been identified as Cry toxin receptors in diverse lepidopteran, coleopteran, and dipteran species.

A 185 kDa cadherin (AdCad1) from larvae of the lesser mealworm (*Alphitobius diaperinus*) larvae was reported as the first identified receptor for Cry3Bb toxin. The AdCad1 protein contains typical structural components for Cry toxin receptor cadherins, including nine cadherin repeats (CR9), a membrane-proximal extracellular domain (MPED) and a cytosolic region. Peptides corresponding to the CR9 and MPED regions bound Cry3Bb toxin with high affinities (23 nM and 40 nM) and significantly synergized Cry3Bb toxicity against *A. diaperinus* larvae.

Silencing of AdCad1 expression through RNA interference resulted in highly reduced susceptibility to Cry3Bb in *A. diaperinus* larvae. The CR9 peptide fed with toxin to RNAi-treated larvae restored Cry3Bb toxicity. These results are evidence that AdCad1 is a functional receptor of Cry3Bb toxin and that exogenously fed CR9 peptide can overcome the effect of reduced AdCad1 expression on Cry3Bb toxicity to larvae.

Abbreviations: cadherin, Cad; alkaline phosphatase, ALP; aminopeptidase N, APN; *Bacillus thuringiensis*, Bt; cadherin repeat, CR; cytoplasmic region, CYTO; membrane proximal extracellular domain, MPED; signal peptide, SP; transmembrane, TM; polymerase chain reaction, PCR; qRT-PCR, quantitative real time PCR.

The subject disclosure relates in part to a cadherin fragment (BtB) that overcomes insect resistance. In studies reported herein, this property of BtB is demonstrated using RNAi interference of cadherin expression of lesser mealworm. Larvae that have lost susceptibility to Cry3Bb become susceptible when BtB is ingested with Cry3Bb.

A beetle cadherin that functions as a 'BtBooster' was cloned from the lesser mealworm. The cloned cadherin differs significantly in sequence from the rootworm cadherin. The lesser mealworm (*Alphitobius diaperinus*) cadherin is distinct from the western corn rootworm cadherin (*Diabrotica virgifera*). This *A. diaperinus* cadherin fragment 'boosts' Cry3Bb toxin activity, which is the toxin used for rootworm control.

Cadherins function as receptors of Cry toxins in Lepidoptera, Coleoptera (beetles), and Diptera (mosquitoes). It has been demonstrated in Lepidoptera that loss of cadherin by mutations in larvae causes resistance to Bt Cry toxins. In beetles, RNAi interference of cadherin expression in midget causes resistance to Bt Cry toxins. In the presently described studies, RNAi was used to knock down cadherin expression in the lesser mealworm. The results indicated that feeding the cadherin fragment reversed the resistance and caused the insects to be killed by Cry3Bb with the cadherin fragment completely overcomes resistance to the Bt Cry toxin. This is the first demonstration that a BtBooster can overcome resistance to a Bt toxin when resistance is due to cadherin loss.

It was previously discovered that fragments of cadherin proteins that function as Bt Cry receptors can synergize Cry toxins. It was investigated how cadherin fragments synergize Cry toxicity to beetles as it applies to the improved control of pest beetle larvae.

BtB is believed to act by binding Bt Cry toxins and possibly protecting them from digestive proteinases in the insect gut lumen. Alternatively, BtB promotes toxin attachment to the brush border membrane. Three BtB proteins that enhance Cry3Aa and Cry3Bb toxicity to Colorado potato beetles and rootworms have been identified, as well as BtB proteins that enhance Cry3Aa, Cry3Bb and Cry8Ca toxicity to lesser mealworm.

Cry toxins such as Cry3Bb, Cry3Aa that are active against rootworms can also kill larvae of the darkling beetle *Alphitobius diaperinus*; these larvae are also called lesser mealworms. Similarly, Cry8Ca, a white grub active toxin, also kills lesser mealworm.

A three cadherin repeat (CR) fragment of *Manduca sexta* cadherin enhances Cry1Ac toxicity to *Helicoverpa zea* 95-fold and a similar three CR fragment of WCRW cadherin enhances Cry3 toxicity to WCRW 10-fold. By characterizing sites on insect cadherin fragments that bind Cry3Bb, and sites on Cry3Bb that bind cadherin fragments, features of both molecules were defined as playing a role for Cry3Bb toxicity to coleopteran pests and toxicity enhancement by cadherin fragments. A cadherin from LMW was also cloned and characterized. Its use as a Cry synergist was analyzed.

Insects in at least three orders (Lepidoptera, Coleoptera and Diptera) can acquire resistance to Cry proteins through loss of midgut cadherin which in susceptible insects would function as Bt Cry receptors. In several species of lepidopteran larvae, resistance has occurred in the field due to insect populations that have reduced amounts of midgut cadherin.

In the laboratory, insect resistance can be induced through the use of RNA interference (RNAi) technology to 'knockdown' cadherin expression and this has been accomplished for coleopteran and dipteran larvae.

Loops on a WCRW-active Cry3Bb toxin that determine binding to a cadherin receptor were characterized. Results from 454 sequencing of midgut cDNA were used to clone LMW midgut cadherin. The binding and synergistic properties of the LMW cadherin peptides were then determined.

Using RNAi knockdown, cadherin expression was inhibited in midgut, resulting in Cry3Bb toxin-resistance in larvae.

Resistance was overcome by feeding a cadherin peptide with a Cry protein (Cry3Bb as exemplified).

Using RNAi interference of a cadherin in beetle larvae, resistance to Cry3Bb was induced. The ability of a cadherin fragment to suppress Cry3Bb resistance indicates for that first time that cadherin fragments may serve as a management tool for insect resistance.

The same types of experiments using RNAi knockdown in rootworms can be used for observing similar BtB effects as for the lesser mealworm.

The subject disclosure also relates in part to the general use of RNAi to show restoration of activity in Cry-resistance situations.

BtBooster Enhancement of Bt Cry Protein Toxicity to Beetle Larvae.

Fragments of cadherins derived from insect midgets enhance *Bacillus thuringiensis* Cry protein toxicity to insect species in at least three orders: Lepidoptera, Diptera, and Coleoptera. Tested cadherins are derived from the caterpillars *Manduca sexta* and *Spodoptera frugiperda*, the mosquito *Anopheles gambiae*, and the beetles *Tenehrio molitor* and *Diabrotica virgifera*.

The Lesser Mealworm, *Alphitobius diaperinus*, and its Potential for Control with *Bacillus Thuringiensis* and BtBooster Combinations.

The lesser mealworm (*Alphitobius diaperinus*) is a beetle in the family Tenebrionidae. Members of the tenebrionid family are commonly called darkling beetles as adults. Many tenebrionid larvae feed on stored grain and are called flour beetles or mealworms. With respect to susceptibility to *Bacillus thuringiensis*, the yellow mealworm *Tenebrio molitor*, a stored grain pest, is susceptible to the Cry3Aa toxin produced by Bt *tenebrionis*. The red flour beetle, *Tribollum castaneum*, is resistant to Bt *tenebrionis* and some other known Bt strains. This is unfortunate from a scientific perspective because many tools including a genomic sequence and RNAi are available for investigation of *T. castaneum*. The lesser mealworm, *Alphitobius diaperinus*, as a serious pest in the poultry production industry, was one focus of this project.

Clone Cadherin from Midgut of Lesser Mealworm.

cDNA was prepared from midgut of lesser mealworm larvae and fragments subjected to next-generation sequencing using a 454 sequencer. Contiguous regions were assembled and regions homologous to known cadherins were identified by BLAST searches. Using techniques of 3' and 5' RACE, the complete DNA region encoding AdCad1 was cloned and sequenced in both directions. The complete nucleotide and amino acid sequence for AdCad1 are provided by SEQ ID NO:1 and SEQ ID NO:2, respectively. AdCad1 protein has a signal peptide, cadherin repeats (CR), a membrane proximal extracellular domain (MPED), a membrane spanning regions and a cytoplasmic domain (see, e.g., FIG. 1A).

AdCad1-CR9 (SEQ ID NO: 4) and AdCad1-MPED (SEQ ID NO: 6) peptides were cloned from the complete AgCad1 DNA using PCR and inserted into pET vector for expression in *E. coli* and produced for testing for BtB function.

Cadherin Sources

Fragments of insect midgut cadherins (from epithelial cells) can be used according to the subject disclosure. Derivatives and variants thereof (including 95% and 99% variants) can also be used according to the subject disclosure. Lesser meal worm cadherins are one type of cadherin exemplified herein. Incorporated by reference are other beetle cadherin sequences that are included in prior applications (such as the DvCad peptides and the TmCad peptide), which can also be used according to the subject disclosure. See for example:

Adang, M. J. Enhancement of *Bacillus thuringiensis* Cry toxicities to lesser mealworm, *Alphitobius diaperinus*. U.S. Patent Application 20110201549. Published Aug. 18, 2011; and Adang, M. J. Abdullah, M. A. F. Enhancement of *Bacillus thuringiensis* Cry protein toxicities to coleopterans, and novel insect cadherin fragments. U.S. Patent Application 20110183896. Published Jul. 28, 2011.

The subject disclosure relates in part to novel fragments of cadherins, e.g., those derived from lesser meal worm. The subject disclosure also relates in part to the use of cadherin fragments (and derivatives and variants thereof) for controlling insects, particularly Cry-resistant insects.

Exemplary AdCad sequences for use according to the subject invention include AdCad1-CR9 (SEQ ID NO:4) and AdCad1-MPED (SEQ ID NO:6). Additional sequences can be used according to the subject invention. For example, the WCRW midgut cadherin was used as a template to generate a cadherin fragment that has a potential toxin binding site. The generated WCRW DvCad1-CR8-10 peptide was expressed in *E. coli* and has the predicted binding site $^{3111}$SSLNVTVN$^{1318}$ (SEQ ID NO: 54), which has similarity to Cry1A toxin binding region 2 (TBR 2) of *Manduca sexta* cadherin. The WCRW cadherin and the DvCad1-CR8-10 cadherin peptide do not include $^{1416}$GVLTLNIO$^{1423}$ (SEQ ID NO: 17), which matches toxin binding region 3 (TBR 3) of *M. sexta* cadherin.

Target Insects

Insects that can be targeted for control according to the subject disclosure include rootworms including corn rootworms, including Western and Southern corn rootworms. Grubs, including those of Japanese beetles, can also be targeted. *Tenebrio* species, such as *Tenebrio molitor*, can also be targeted, as *Alphitobius* species, such as *Alphitobius diaperinus*.

In corn, rootworms, European corn borers, and armyworms can be targeted according to the subject disclosure. In cotton, bollworm is one primary insect to be targeted according to the subject disclosure.

Lesser meal worms have similarities to rootworms and Japanese beetle larvae, for example.

Resistant insects of all of these types can be used and targeted according to the subject disclosure.

Cry Proteins

Cry3B, particularly Cry3Bb, is one Cry protein that can be used according to the subject disclosure. Cry34 and Cry35 proteins can also be used according to the subject disclosure. See the website at lifesci.sussex.ac.uldhome/Neil_CrickmoreiBt/ for a list of Cry proteins.

Transgenic Plants and Reduced Refuge

Transgenic plants can be used according to the subject invention. That is, plants can be engineered to express and produce combinations of BtBs and Cry proteins as disclosed and suggested herein. Plant cells that produce such BtBs and Cry proteins are included.

According to the subject invention, required refuge for various crops (such as corn) can be reduced. Such refuge can be 40%, 30%, 20%, 10%, 5%, and even zero (percent of refuge crop to transgenic crop), for example, due to the resistance management techniques provided by the subject disclosure. Similarly, seed mixtures with these percentages (and others) can be produced accordingly.

Summary of Results Presented Below

AdCad1 was identified as a receptor of Cry3Ba toxin in *A. diaperinus* (Coleoptera: Tenebrionidae). This result is consistent with cadherin (TmCad1) receptor function for Cry3Aa in *T. molitor*, and Cry3Ba in *T. castaneum* (Contreras et al., 2013; Fabrick et al., 2009). As analyzed to date, insect cadherins with Cry receptor function have a high-affinity toxin binding site in the CR region nearest the plasma membrane (Fabrick et al., 2009; Hua et al., 2004; Hua et al., 2013; Xie et al., 2005). The CR9 region of AdCad1, which bound Cry3Bb with a $K_d$=23.2 nM and synergized toxicity to larvae, has an amino acid sequence similar to Cry1A binding sites in *M. sexta* and *H. virescens* and Cry3 binding sites in TmCad1 and TcCad1. It was proposed that amino acid sequences in loops of Cry toxins bind cadherin via hydropathical complementarity (Gomez et al., 2002). The pattern of amino acid hydrophobicity in the 'putative' binding site of AdCad1-CR9 is similar to that for known binding sites for MsBtR1, HvCad and TmCad1 (Table 1).

TABLE 1

Alignment of Cry toxin binding motifs from insect cadherins.

| Cadherin Region | Binding Region | Reference | SEQ ID NO: |
|---|---|---|---|
| MsBtR1-CR12 | $^{1416}$GVLTLNIQ$^{1423}$ | (Chen, Hua et al. 2007) | 17 |
| HvCad1-CR11 | $^{1423}$GVLTLNFQ$^{1430}$ | (Xie, Zhuang et al. 2005) | 18 |
| TcCad1-CR12 | $^{1361}$GVIKYNFK$^{1369}$ | (Contreras, Schoppmeier et al. 2013) | 19 |
| TcSSS | $^{1115}$GSATVELK$^{1122}$ | (Contreras, Schoppmeier et al. 2013) | 20 |
| TmCad 1-CR12 | $^{1359}$GDITINFE$^{1366}$ | (Fabrick, Oppert et al 2009) | 21 |
| AdCad 1-CR9 | $^{1273}$GKVTLNKP$^{1280}$ | (this study) | 22 |
| AdCad 1-MPED | $^{1391}$GEISAQIQ$^{1398}$ | (this study) | 23 |

Unexpectedly, AdCad1-MPED also bound Cry3Bb with high affinity ($K_d$=40.6 nM) and synergized Cry3Bb toxicity. An 8-aa motif ($^{1391}$GEISAQIQ$^{1398}$; SEQ ID NO: 23) within AdCad1-MPED is conserved relative to MsBtRI binding motif ($^{1416}$GVLTLNIQ$^{1423}$; SEQ ID NO: 17) (Table 1). In addition, AdCad1-MPED has a stretch of amino acids ($^{1391}$GEISAQIQ$^{1398}$; SEQ ID NO: 23) with some similarity to Cry binding sites in lepidopteran and coleopteran cadherins (Table 1). As Cry loop regions do not require conserved amino acids (Fujii et al. 2013) for cadherin receptor binding, possibly the exact amino acid sequence at the Cry-binding site is not as important as the hydrophobicity of several amino acids.

The ability of AdCad1-CR9 and -MPED peptides to synergize Cry3Bb larval toxicity is consistent with the correlation between the ability of a cadherin peptide to bind to toxin with high-affinity and enhance larval toxicity (Chen et al., 2007; Fabrick et al., 2009; Hua et al., 2008; Park et al., 2009; Peng et al., 2010). The report of increased Cry3Aa toxicity to three vegetable beetles by Tm-TBR is notable for the high level of toxicity enhancement (Gao et al., 2011). But it is interesting that the ratio of Cry3Ba to AdCad1 peptides saturated for toxicity synergism at a lower ratio than Cry:Cad peptide combinations saturated in Lepidoptera (Chen et al., 2007). Similar results were reported by Gao et al., where synergism of Cry3Aa was saturated at a 1:5 ratio of Cry3Aa:Tm-TRR (Gao et al., 2011). The same Tm-TBR peptide was shown to increase oligomerization of Cry toxin (Fabrick et al., 2009), a property previously reported for MsCad1 synergistic peptides (Pacheco et al., 2009). Recently, a peptide containing the Cry3Ba binding site of *T. castaneum* sodium solute transporter was reported as a Cry synergist (Contreras et al., 2013). Interestingly, the Cry binding site on sodium solute transporter (Table 1) is similar to the cadherin binding sites also listed in Table 1, and the site is in the region of the protein with a cadherin repeat-like structure.

Diverse proteins have been proposed as functional receptors for Cry3 toxins in tenebrionid species Similar to the present findings, Fabrick et al (Fabrick et al., 2009) demonstrated a functional role for a cadherin from *T. molitor* and a peptide derived from this cadherin enhanced Cry3A toxin oligomerization and toxicity against diverse beetle pests (Gao et al., 2011). More recently, a sodium solute symporter from *T. castaneum* (TcSSS) (Contreras et al., 2013) and a GPI-anchored alkaline phosphatase from *T. molitor* (Zuniga-Navarrete et al., 2013) have been proposed as functional receptors for Cry3Ba and Cry3Aa toxins, respectively. In the present AdCad1 silencing experiments, a positive correlation was identified between reduced AdCad1 transcript levels and reduced susceptibility to Cry3Bb. In some insect species, several cadherin genes have been identified, and in some cases all of them have been reported as involved in Cry intoxication (Ikawa et al., 2000). Zhang et al. recently reported that midgut cadherins in *Trichoplusia ni* were characterized of sequence variation and differential splicing (Zhang et al., 2013) In *A. gambiae*, two cadherins were evidenced to bind Cry4Ba and Cry11Ba separately (Hua et al., 2013; Hua et al., 2008).

The instant data identify AdCad1 as a functional Cry3Bb receptor in Coleoptera. A sodium solute symporter protein from *T. castaneum* had been identified as a receptor for Cry3Ba toxin previously (Contreras et al., 2013). In another Cry3Bb-susceptible coleopteran, *D. virgifera virgifera*, a cadherin protein was proposed as putative Cry3Bb receptor (Park et al, 2009). However, AdCad1 appears very different from DvvCad or from the Cry3Aa receptor TmCad (Fabrick et al., 2009). The instant discovery of two peptides that enhance Cry3Bb toxicity and restore Cry toxicity in cadherin-silenced may have important applications in control of coleopteran larvae and resistance management.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Example 1—Materials and Methods

1.1 Insects

A colony of *Alphitobius diaperinus* (Coleoptera: Tenebrionidae) was founded from adult beetles. The *A. diaperinus* colony was kept in containers and maintained on pine shavings and chicken feed (Layena, Purina Mills) with apple slices at 28° C. and 70% relative humidity with a photoperiod of 16 h of light and 8 h of darkness.

1.2 Preparation of Cry Toxin

A previously reported construct (Park et al., 2009) producing Cry3Bb protein in *Escherichia coli* BL2I (DE3)/pRIL (Stratagene, La Jolla, Calif.) was cultured in LB medium supplemented with kanamycin antibiotic at 37° C. with continuous shaking at 250 rpm. The Cry3Bb protein was over-expressed by induction with 1 mM of isopropyl β-D-thiogalactopyranoside (IPTG) when the cultures reached 0.6-0.7 at $OD_{600}$ and cells were harvested after 12 hr of additional culture. The Cry3Bb toxin was purified as described elsewhere (Park et al., 2009). The final Cry protein concentration was determined from a Coomassie-stained SDS-10% gel based on band density as determined by gel image analyzer (Alpha Innotech, San Leandro, Calif.) using bovine serum albumin (BSA) as a standard.

1.3. Cloning of AdCad.1

Midguts were dissected from *A. diaperinus* 4th instar larvae for total RNA extraction as described elsewhere (Hua et al., 2008). Total RNA was prepared using the RNeasy Mini kit (Qiagen) from 120 mg fresh midgut. The cDNA was synthesized from 5 µg of total RNA using reverse transcriptase (Gihco-BRL) and fragments subjected to next-generation sequencing using a 454 sequencer (454 Life Sciences) at the Molecular Genetics Instrumentation Facility (University of Georgia). Sequence samples were assembled by MIRA3 (Creative Commons, San Francisco, Calif., USA). Thirty of the assembled contigs were identified as cadherin-like using BlastX of NCBI (website: ncbi.nlm.nih.gov).

Due to the highest identity between c224 contig and TmCad1, the full length AdCad1 cDNA was prepared using pyro-sequence of c224 to design primers to clone the internal c224 region of AdCad1 and then the 5' and 3' ends using a RACE kit (SMARTer RACE cDNA Amplification, Clontech) following manufacturer's instructions. Primers Ad1 to Ad18, used in the cloning of AdCad 1 cDNA and constructing sub-clones, are listed in Table 2.

TABLE 2

Nucleotide primers used for cloning AdCad1.

| Primer | Orientation | Position | Primer DNA Sequence (5' to 3') | SEQ ID NO: |
|---|---|---|---|---|
| Ad1 | Forward | 4577-4604 | AAATCCGATGAAATTACAACAGCAACC G' | 24 |
| Ad2 | Forward | 4615-4646 | GAATCTTAAACAACAGAAACCAGTAAATAAAG | 25 |
| Ad3 | Reverse | 4615-4646 | CTTTATTTACTGGTTTCTGTTGTTTAAGATTC | 26 |
| Ad4 | Reverse | 4689-4716 | CCCTCTGCTAAGAAAGCTGATCTCATAC | 27 |
| Ad5 | Forward | 1937-1964 | GGGTCTACGATTAAGGTGAATGAAA ACC | 28 |
| Ad6 | Forward | 1973-2001 | GGTGCCTCACTCGAAGCGGATATUCTGC | 29 |
| Ad7 | Reverse | 2267-2291 | CGGAATCACTTTCTTGTCCGGAGAC | 30 |
| Ad8 | Reverse | 2143-2170 | CTTGGCTTTAACTTGATTTCGMTCCG | 31 |
| Ad9 | Forward | 3618-3648 | CGCACATATGACCGAAATGATATACAAGCT | 32 |
| Ad10 | Reverse | 4072-4103 | AATCCTCGAGCATTACAGGAGCATGGTCGTTA | 33 |
| Ad11 | Forward | 4084-4111 | TCCTCATATGGATTCCGATTCTTACATT | 34 |
| Ad12 | Reverse | 4759-4790 | TAAGCTCGAGCGTTAAAATCTCCTCCATATCT | 35 |
| Ad13 | Forward | 93-121 | GATCAGTAGGGTAATACAAGATGAAGCTC | 36 |
| Ad14 | Forward | 1666-1687 | GCAACTGATGCGGACGCAGTGG | 37 |
| Ad15 | Forward | 3437-3460 | AAAGTCAAGAGCCTAACAGCAGAC | 38 |
| Ad16 | Reverse | 5102-5133 | AAATAACATTAAACTTAATTCTCTTCT1CTGC | 39 |
| Ad17 | Reverse | 3496-3519 | GTAGTGGATGATGGACAAAAGGGG | 40 |
| Ad18 | Reverse | 1924-1951 | GGGTCCACGATTAAGGTGAATGAAAACC | 41 |

The resulting three PCR products were cloned into pGEM-Teasy TA-cloning vector (Promega) and inserts were sequenced in both forward and reverse directions (Macrogen USA). To confirm that these over-lapping cadherin regions were from the same gene we amplified the complete open reading frame (ORF) from midgut cDNA using primers Ad13 and Ad16 (Table 2). Another four overlapping regions of AdCad1 cDNA were amplified using primers Ad13 to Ad18 with different primer combinations. All five PCR products were cloned into the pGEM-Teasy vector. The cDNA sequence for the AdCad1 ORF in clone pGEM-AdCad1 and the sequences from the 4 cloned sub-regions were identical and submitted to GenBank as accession number KC470207. Predicted AdCad1 cadherin repeats were identified by the program ISREC ProfileScan server (website: hits.isb-sib.chicgi-bin/PFSCAN). Clustal W (version 2.1) at website: genome.jp/tools/clustalw/ was used to compare AdCad1 with other cadherins from different species.

1.4 Expression of Truncated AdCad1 Fragments

The regions of pGEM-AdCad1 encoding CR9 (residues 1173 to 1327; SEQ ID NO:4) and MPED (residues 1328 to 1556; SEQ ID NO:6) were amplified using primers Ad9/Ad10 and Ad11/Ad12 (Table 2), respectively. The PCR products were purified with a Qiaex II gel extraction kit (Qiagen) and cleaved with Nde I and Xho I restriction enzymes. The digested amplicons were cloned into the pET-30a expression vector (Novagen) yielding pET-Ad-Cad1-CR9 and pET-AdCad1-MPED, respectively. Both cloned plasmids were sequenced in both directions to confirm correct insertion and fidelity of the AdCad1 reading frame. The AdCad1 peptides with a C-terminal His-tag from the pET-30a vector were over expressed by induction with 1 mM isopropyl β-D-thiogalactopyranoside after the plasmids were transformed into $E.\ coli$ strain BL21-CodonPlus (DE3)/pRIL. The culture was harvested 4 hours after induction. For binding affinity experiments, the expressed AdCad1-CR9 and AdCad1-MPED peptides were purified from inclusion bodies on a HiTrap NI2-chelating HP column (GE Healthcare, Piscataway, N.J.) according to Chen et al (Chen et al., 2007).

1.5 Insect Bioassay

Bioassays were conducted on a semi-solid chicken feed diet. The chicken feed diet consisted of 1.45% (w/v) agar (Bio-Serv) and 14.4% (w/v) chicken feed (Layena, Purina Mills) in distilled water. Feed pellets were chopped with a bladed coffee grinder and then ground with a ceramic mortar and pestle before mixing with agar in water. The mixture was heated just to boiling in an autoclave, blended and then 1 ml of diet mixture was dispensed into each well of a 128-well bioassay tray (C-D International, Pitman, N.J.) by syringe. Cry3Bb toxin or toxin plus AdCad1-CR9 or AdCad1-MPED peptides were serially diluted with sterile deionized water and then overlaid onto the diet surface and air-dried. One third-instar larva was transferred into each well; the trays were sealed with perforated lids (C-D International, Pitman, N.J.) and then covered with brown paper to provide a dark environment. Each bioassay was conducted with 16 larvae per replicate and two replicates per concentration. The trays were incubated at 28° C. for 3 days before mortality counts were determined. The optimal ratio of Cry3Bb to AdCad1-CR9 or AdCad1-MPED peptide was determined by performing bioassays with a fixed concentration of Cry toxin (10 µg/cm$^2$) and an increasing amount of AdCad1-CR9 or AdCad1-MPED (i.e., 1:0, 1:1, 1:10, and 1:100 mass ratios of Cry3Bb: cadherin peptide). A 1:10 mass ratio is equivalent to a 1:30 molar ratio for AdCad1-CR9 and a 1:25 molar ratio for AdCad1-MPED. For bioassays testing larvae treated with dsRNA, a fixed concentration of Cry3Bb toxin (100 µg/cm$^2$) was used either alone or in combination with a 1:10 mass ratio of Cry3Bb: AdCad1-CR9 peptide.

1.6 Silencing of AdCad 1 Expression with RNA Interference

Plasmid pGEM-AdCad1 was used as a template for amplification of two partial AdCad1 regions (nt: 327 to 757 and 4308 to 4720) by PCR with primers Ad19 & Ad20, and Ad23 & Ad24 (Table 3), respectively.

TABLE 3

Nucleotide primers used for dsRNA synthesis and qRT-PCR amplification of AdCad1 and AdCadRPS6.

| Primer | Orientation | Position | Primer DNA Sequence (5' to 3') | SEQ ID NO: |
|---|---|---|---|---|
| Ad19 | Forward | 324-343 | TATCAGGGAATACCTACCCG | 42 |
| Ad20 | Reverse | 737-757 | CAGTGTCAGATAAACCTCAGC | 43 |
| Ad21 | Forward | 324-343 | taatacgactcactatagggTATCAGGGAATACCTACCCG | 44 |
| Ad22 | Reverse | 518-537 | taatacgactcactatagggGACAAAGTTGGGCTCTCATC | 45 |
| Ad23 | Forward | 4308-4328 | CAGCGAATCTTAGTAAATGGG | 46 |
| Ad24 | Reverse | 4700-4720 | GCTTTCTTAGCAGAGGGTTTA | 47 |
| Ad25 | Forward | 4308-4328 | taatacgactcactatagggCAGCGAATCTTAGTAAATGGG | 48 |
| Ad26 | Reverse | 4549-4567 | taatacgactcactatagggGCCTTGTACAGTGGCTACG | 49 |
| AdCad 1/qPCR-f | Forward | 4936-4956 | GGCAGCTCCTACCACTAACAA | 50 |
| AdCad 1/qPCR-r | Reverse | 504-5061 | ATGCCAATCAACTCGGAACCT | 51 |
| AdRPS6/qPCR-f | Forward | 561-580 | CCCAAAATTCAGCGTCTCAT | 52 |
| AdRPS6/qPCR-r | Reverse | 608-627 | TCTTCAAGGCCAACCTATGG | 53 |

Each PCR product was used as a template for a second PCR using region-specific primers tailed with the T7 polymerase promoter sequence (Ad21 & Ad22, and Ad25 & Ad26, respectively). After the amplicons were confirmed by sequencing, dsRNA-1 and dsRNA-2 were synthesized in vitro with the Ambion MEGAscript high yield transcription kit (Applied Biosystems/Ambion, Austin, Tex.) according to the manufacturer's protocols. Purified dsRNAs were quantitatively determined by NanoDrop (N-1000) spectrophotometer and stored at ~20° C. until injected in *A. diaperinus* larvae.

Fourth instar *A. diaperinus* larvae were anesthetized on ice for 5-7 min before ventral injection with dsRNA. Control larvae were injected with ~1 µl of GFP-dsRNA (n=68). Experimental larvae were injected with either of the two AdCad1-dsRNAs using Hamilton 10 µl microliter syringe (~75 ng/larva; n=72 for larvae group #1 and n=78 for group #2; dsRNA correspond to locations at the 5'-end or 3'-end of AdCad1 cDNA respectively). After injection, the larvae were reared on diet without toxin under standard rearing conditions for three days (72 h) or six days (144 h).

1.7 Quantitative RealTime PCR

Three or six days after injection, larvae were evaluated for AdCad1 transcript levels by quantitative real-time PCR (qRT-PCR). Three larval guts from each injection group were separately dissected. Each individual gut was soaked in 200 µl of TRIzol reagent (Ambion) in a microfuge tube, homogenized with a cordless motor-driven pellet pestle (Grainger) and centrifuged at 12,000×g for 30 min at 4° C. The supernatant was collected and mixed, shaking vigorously with 40 µl of chloroform. The mixture was set at room temperature for 5 min and centrifuged as above for 15 min at 4° C. The upper aqueous phase containing RNA was collected to a new tube and mixed with the same volume of 100% isopropanol. After incubation at room temperature for 10 min, the mixture was centrifuged at 12,000×g for 10 min at 4° C. The RNA pellet was washed with 75% ethanol, air dried and dissolved in 50 µl of RNase-free water. The total RNA amount was determined with NanoDrop Spectrophotometer (N-1000).

The cDNA was synthesized with SuperScript III First-Strand Synthesis System (Invitrogen) using 5 µg of total RNA as template. The resulting cDNA was diluted 100-fold for qRT-PCR. iQ SYBR Green Supermix (Bio-Rad) primers were added as follows: AdCad1/qPCR-f and AdCad1/qPCR-r for AdCad1 expression or AdRPS6/qPCR-f and AdRPS6/qPCR-r for the endogenous control ribosomal protein S6 (RPS6), selected based on 454 pyrosequencing data. Primers (Table 3) were designed using software available at the website Frodo.wi.mit.edu. Relative percentages of gene silencing were calculated from three biological replicates for each injection treatment using RPS6 to normalize gene expression by the $2^{-\Delta\Delta C_T}$ method.

Eight days post-injection, larvae from the control (GFP-dsRNA) and experimental group (AdCad1-dsRNA #1 and #2) were bioassayed as described in the bioassay section. The injected larvae were put on diet coated 100 µg/cm$^2$ of Cry3Bb inclusion bodies with or without AdCad1-CR9 or AdCad1-MPED purified peptides. The mortality was scored on the eighth day of bioassay, 16 days after dsRNA injection.

1.8. Microliter Plate Binding Assays

To determine the binding affinity of Cry3Bb toxin to AdCad1-CR9 and AdCad1-MPED peptides, an enzyme-linked immunosorbent assay (ELISA) was performed as described elsewhere (Park et al., 2009). Purified cadherin peptides were biotinylated using a 50-fold molar excess of sulfo-NHS (N-hydroxysuccinimide)-photocleavable biotin (Pierce, Rockford, Ill.) according to the manufacturer's manual. The final reaction was dialyzed against 200 mM NaCl, 20 mM $Na_2CO_3$ (pH 8.0) and stored in aliquots at 4° C. until needed for the binding assays. The microtiter plates (high-binding, 96-well Immulon 2HB plates; Thermo Fisher Scientific, Inc.) were coated with chymotrypsin activated 1.0 μg Cry3Bb/well in 50 μl coating buffer (100 mM Na2CO3, pH 9.6) overnight at 4° C., then biotin labeled AdCad1 peptides were incubated with or without a 1,000-fold molar excess of unlabeled AdCad1-CR9 or AdCad1-MPED peptides. After washing, the plate was incubated with horse radish peroxidase-conjugated streptavidin (SA-HRP; Pierce), then incubated with HRP chromogenic substrate (1-Step Ultra TMB-ELISA, Thermo Fisher Scientific, Inc.) to quantify the bound peptides. Color development was stopped by adding 2M sulfuric acid, and absorbance was measured at 450 nm using a microplate reader (MDS Analytical Technologies, Sunnyvale, Calif.). The binding data from replicated experiments done with triplicate samples were analyzed using Sigma Plot software Version 11.0 (SPSS Science, Chicago, Ill.) to determine the best site model fit.

Example 2—Results 2.1 Cloning and Analysis of *A. Diaperinus* Cadherin cDNA

From a de novo assembly of a 454 sequencing run with *A. diaperinus* midgut cDNA, 80,000 contigs were obtained. Thirty were identified as partial genes belonging to the cadherin family by BlastX computation. After manual analysis, these 30 contigs were assembled into two cDNAs. The full length 5,208 nt cDNA encoding *A. diaperinus* cadherin-1 (AdCad1) was obtained (SEQ ID NO:1).

The AdCad1 ORF encodes a predicted protein of 1,673 amino acids with a calculated molecular mass of 185,325 Da. Hydrophobic regions at the N-terminus and near the C-terminus correspond to a signal peptide and a transmembrane domain (TM), respectively (FIG. 1A). The extracellular domain consists of nine cadherin repeats (CR) and a membrane-proximal extracellular domain (MPED) joining CR9 to the TM domain. Alignment by ClustalW indicates 46% identity between full-length AdCad1 and cadherins in the tenebrionida *T. molitor* and *T. castanewn*. There is lower amino acid identity (23-26%) between AdCad1 and cadherins from the coleopteran (*D. v. virgifera*) and lepidopterans *M sexta* and *H. virescens*. AdCad1 also has lower identities (15-21%) with cadherins from mosquito species.

2.2 Binding of AdCad1-CR9 and AdCad1-MPED Peptides to Cry3Bb

The last CR region of cadherin in susceptible insects was revealed to be the critical binding and functional domain for Bt Cry toxins (Fabrick et al., 2009; Hua et al., 2004; Hua et al., 2008). Accordingly, selected CR9 of AdCad1 was selected as a potential candidate repeat for binding assays, and MPED as a comparison. An ELISA assay was used to test for binding of Cry3Bb to heterologously expressed and purified CR9 and MPED peptides (FIG. 1B). In these assays, both biotin-labeled AdCad1-CR9 and AdCad1-MPED peptides specifically and saturably bound to Cry3Bb toxin (FIGS. 2A and 2B). The best fit obtained for the binding data was for a one-site saturation binding model with high affinity ($K_a$=23.2 nM and 40.6 nM for AdCad1-CR9 and AdCad1-MPED, respectively).

2.3 Bioassays of AdCad1-CR9 and -MPED with Cry3Bb in *A. diaperinus* Larvae

Figure 3:
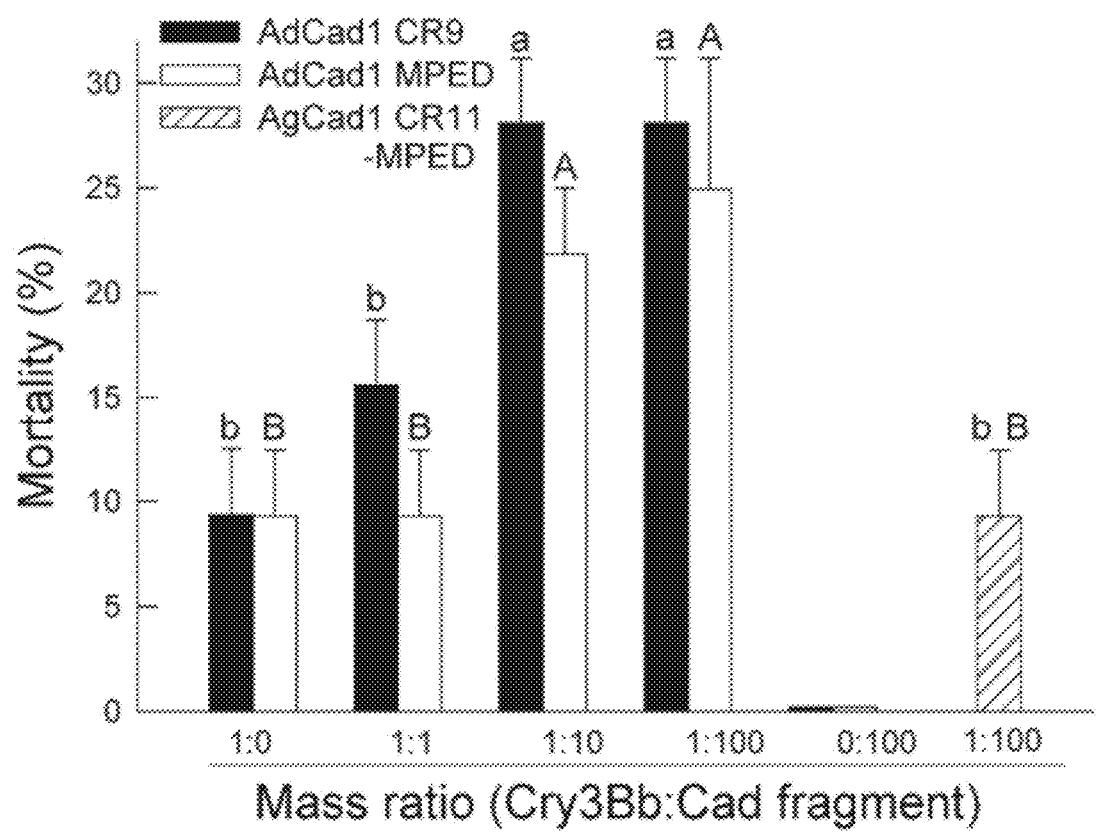
FIG. 3 is a bar graph indicating the synergistic effect of AdCad1 peptides on Cry3Bb toxicity. Cry3Bb inclusion (10 µg/cm$^2$) was used alone or with AdCad1-CR9 or AdCad1-MPED inclusions in various toxin/peptide mass ratios. Each bioassay was conducted with 16 third instar lesser mealworm larvae per replicate and two replicates per concentration. Larval mortality was recorded on day 3. Each data point represents the mean±standard error of the results bioassays. A significant difference (chi-square analysis; $P<0.05$) between larval mortality with Cry3Bb treatment alone and that with Cry3Bb plus peptide treatment at the same toxin dose (A vs B and a vs b).

As previous reports have demonstrated that cadherin-derived peptides from coleopteran species can enhance activity of Cry3 toxins (Park et al., 2009), bioassays testing whether AdCad1 peptides could enhance Cry3Bb toxicity against *A. diaperinus* larvae were performed. Both peptides were able to significantly increase mortality (P<0.005) of Cry3Bb from 10% (toxin alone) to >25% (at a 1:10 mass ratio), while no toxicity was detected in bioassays with peptide alone (FIG. 3). In contrast, a peptide derived from the *Anopheles gambiae* cadherin (AgCad1-CR11-MPED) containing a Cry4B a toxin binding region (Hua et al., 2008) did not affect Cry3Bb toxicity at the 1:100 mass ratio.

Figure 4:
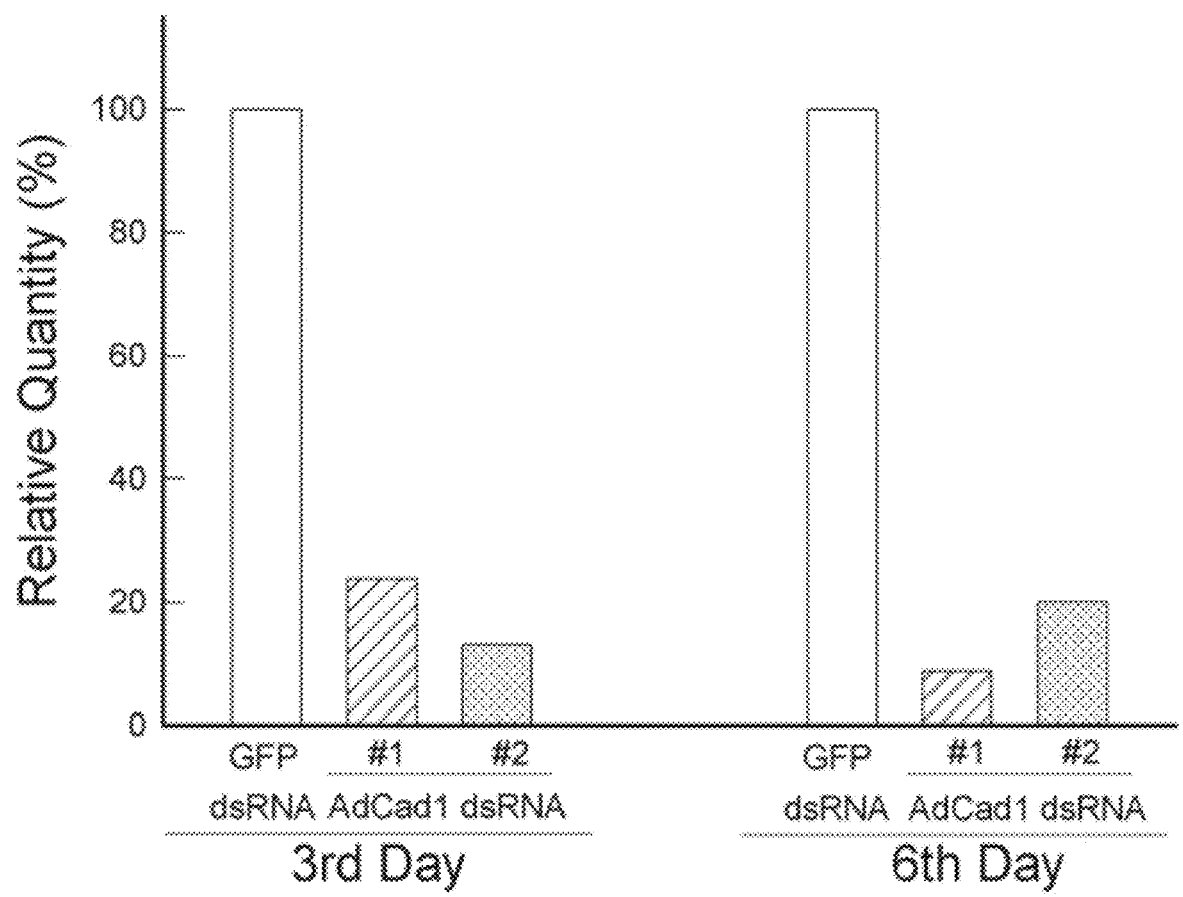
FIG. 4 is a bar graph indicating knockdown of AdCad1 expression in lesser mealworm. The dsRNAs, dsGFP, dsAdCad1-#1 and -#2 were synthesized as described in materials and methods. The relative amount of AdCad1 transcript in each treatment group was compared to that of GFP-dsRNA after normalization to the expression of AdRPS6.

2.4 RNA Interference Knockdown of AdCadl Decreases Cry3Bb Toxicity to *A. diaperinus* Larvae RNA interference was performed to assess the in vivo functional role of AdCad1 as a Cry3Bb receptor. Fourth instar *A. diaperinus* larvae were injected with either GFP-dsRNA as a control or two AdCadl-specific dsRNAs targeting the 5' (214 nt) and 3' (260 nt) AdCad regions, respectively. To test whether the dsRNAs reduced AdCadl expression, the levels of AdCad1 transcripts were measured at 72 h and 144 h post-injection by qRT-PCR. The level of AdCadl transcripts was significantly (P<0.001) reduced in larvae injected with either AdCad1-dsRNA compared with the GFP-dsRNA control (FIG. 4). On the third day post-injection (72 h), the AdCadl transcript levels in larvae injected with AdCadl-specific dsRNAs were decreased to 23.8% and 13.0% compared to the levels in control treatment, and remained low (8.8% and 20.1%, respectively) on the sixth day post-injection (144 h) (FIG. 4).

Figure 5A:
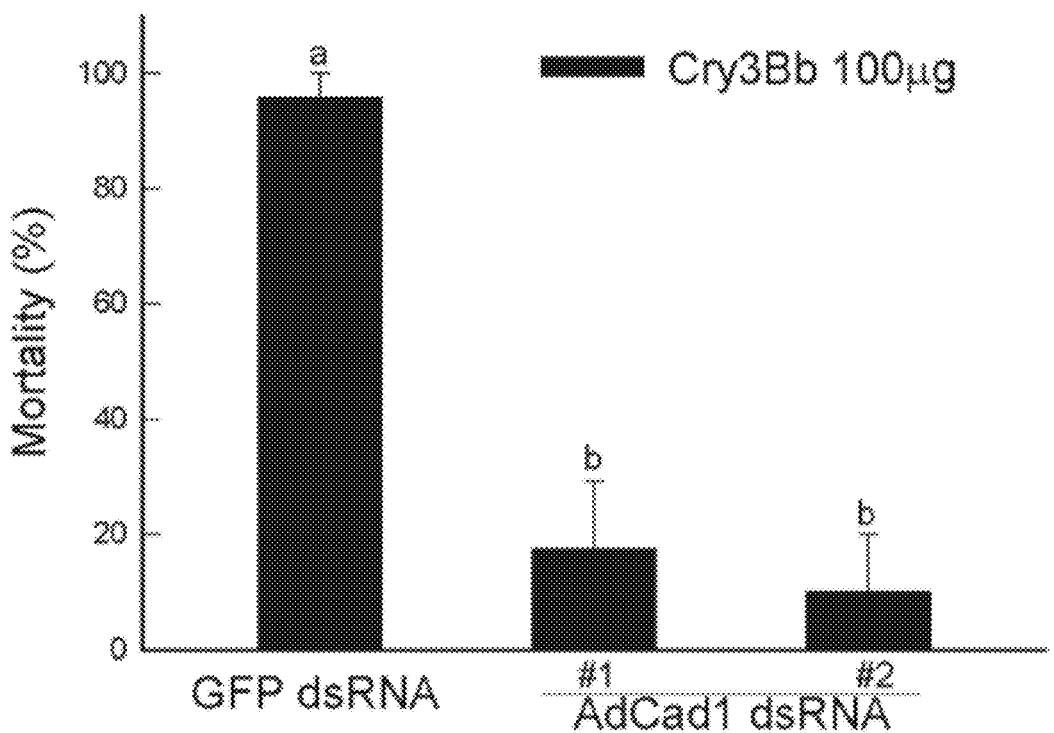
FIG. 5A is a bar graph indicating toxicities of Cry3Bb with or without AdCad1-CR9 peptide on *A. diaperinus* larvae injected dsRNA. Eight days post-injection, larvae from the control (GFP-dsRNA) and experimental group (AdCad1-dsRNA #1 and #2) were bioassayed. Bioassays were performed with a fixed amount of Cry3Bb toxin (100 µg/cm$^2$) at three different times. Larval mortality was recorded on day 3. Each data point represents the mean±standard error of the results from bioassay. A significant difference (chi-square analysis; $P<0.05$) presented between larval mortality with dsGFP and dsAdCad1 (a vs b).
Figure 5B:
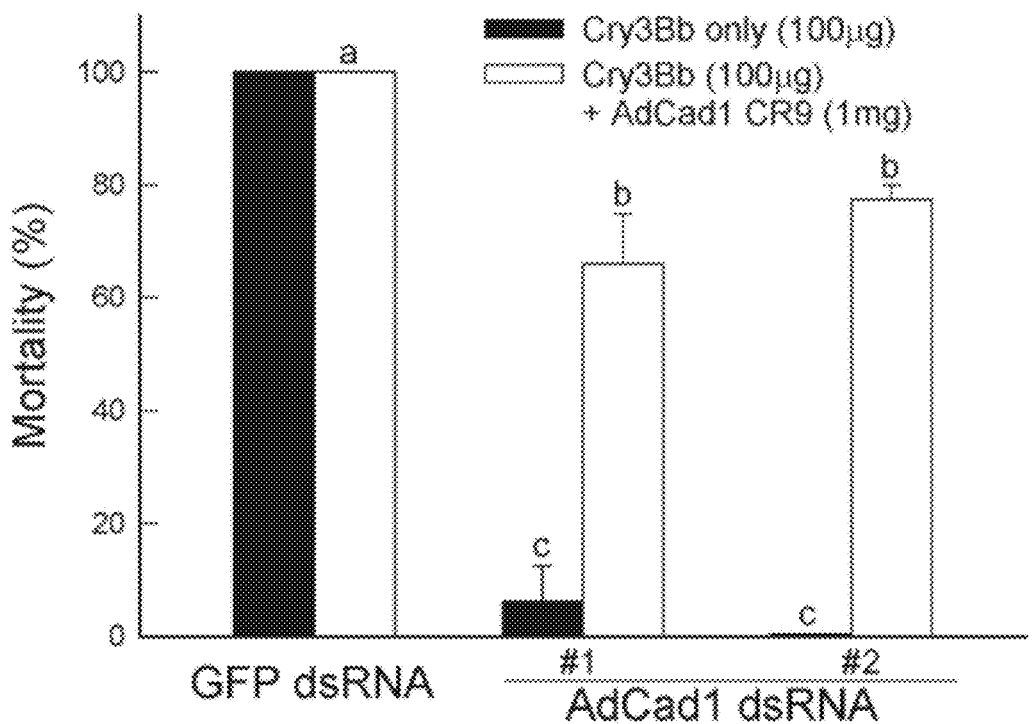
FIG. 5B is a bar graph indicating toxicities of Cry3Bb with or without AdCad1-CR9 peptide on *A. diaperinus* larvae injected dsRNA. The lesser mealworm larvae were injected dsRNA as in FIG. 5A, then bioassayed on Cry3Bb-containing diet with or without 10-fold mass ratio of AdCad1-CR9 inclusion body. Larval mortality was recorded on day 3. Each data point represents the mean±standard error of the results from bioassay. Larval mortality with AdCad1-CR9 inclusions was significantly higher (chi-square analysis; $P<0.001$) than those without AdCad1-CR9 (b vs c) and also significantly differed (chi-square analysis; $P<0.05$) from dsGFP injected larvae (b vs a).

To test the functional Cry3Bb receptor role for AdCad1, *A. diaperinus* larvae were exposed eight days after injection with GFP-dsRNA, or AdCadl-dsRNA #1 or #2 to diet with 100 μg/cm² of Cry3Bb inclusion body on the surface. Mortalities were recorded on the third day (FIG. 5A). About 97% of the GFP-dsRNA injected larvae died, while only 8% and 11% of larvae injected with AdCadl-dsRNA #1 or #2, respectively (P<0.05), were found dead. This observation was positively correlated with the decreasing amount of AdCadl transcript in injected larvae (FIG. 4) which demonstrated AdCadl playing an important Cry 3Bb receptor function during intoxication of *A. diaperinus* larvae. In a subsequent experiment, batches of larvae injected with GFP-dsRNA or AdCadl-specific dsRNAs were randomly divided into two treatment groups. The first group was exposed to 100 μg/cm² of Cry3Bb, resulting in mortality similar to that observed in previous bioassays (compare FIGS. 4 and 5A). The second group of larvae was exposed to diet with 100 μg/cm² of Cry3Bb plus a 1:10 mass ratio of AdCad 1-CR9 peptide on the surface. While the mortality for larvae injected with GFP-dsRNA remained at about 100% with the Cry3Bb:CR9 combination, larval mortality was significantly increased to 60% and 66% (P<0.001) when larvae injected with AdCad1-specific dsRNA were exposed to Cry3Bb:CR9 (FIG. 5B). However, the addition of the AdCadl peptide did not completely restore susceptibility to Cry3Bb in larvae, as larval mortality was statistically different (P<0.05) from GFP-dsRNA fed larvae.

REFERENCES

Adang, Mi., 2011. Enhancement of *Bacillus thuringiensis* Cry toxicities to lesser mealworm *Alphitobius diaperinus*. U.S. application Ser. No. 13/056,380, US Patent Application 20110201549, Published 18 Aug. 2011.

Adang, M. J. Abdullah, M. A. F. Enhancement of *Bacillus thuringiensis* Cry protein toxicities to coleopterans, and novel insect cadherin fragments. U.S. Patent Application 20110183896. Published Jul. 28, 2011.

Braden, C. R., 2006. *Salmonella enterica* serotype *Enteritidis* and eggs: a national epidemic in the United States. Clin. Infect. Dis. 43, 512-517.

Bravo, A., Likitvivatanavong, S., Gill, S. S., Soberon, M., 2011. *Bacillus thuringiensis*: A story of a successful bioinsecticide. Insect Biochem. Mal. Biol. 41, 423-431.

Chen, J., Hua, G., Jurat-Fuentes, L L., Abdullah, M. A., Adang, M. J., 2007. Synergism of *Bacillus thuringiensis* toxins by a fragment of a toxin-binding cadherin. Proc. Natl. Acad. Sci. U.S.A 104, 13901-13906.

Contreras, E., Schoppmeier, M., Real, M. D., Rausell, C., 2013. Sodium solute symporter and cadherin proteins act as *Bacillus thuringiensis* Cry3Ba toxin functional Receptors in *Tribolium castaneum*. J. Biol. Chem. 288, 18013-18021.

Fabrick, J., Oppert, C., Lorenzen, M. D., Morris, K., Oppert, B., Jurat-Fuentes, J. L_, 2009. A novel *Tenebrio molifor* cadherin is a functional receptor for *Bacillus thuringiensis* Cry3Aa toxin. J. Biol. Chem. 284, 18401-18410.

Frankenhuyzen, V. K., 2009. Insecticidal activity of *Bacillus thuringiensis* crystal proteins. J. Invertebr. Pathol. 101, 1-16.

Fujii, Y., Tanaka, S., Otsuki, M., Hoshino, Y., Endo, H., Sato, R., 2013. Affinity maturation of Cryl Aa toxin to the Bomhyx mori cadherin-like receptor by directed evolution. Mol. Biotechnol. 54, 888-899.

Gao, Y. L., Jurat-Fuentes, J. L., Oppert, B., Fabrick, J. A., Liu, C. X., Gao, J. H., Leia, Z., 2011. Increased toxicity of *Bacillus thuringiensis* Cry3Aa against *Crioceris* quatuordecimpunctata, *Phaedon brassicae* and *Colaphellus bowringi* by a *Tenebrio molitor* cadherin fragment. Pest Manag. Sci. 67, 1076-1081.

Gomez, L, Miranda-Rios, J., Rudino-Pinera, E., Oltean, D. L, Gill, S. S., Bravo, A., Soberon, M., 2002. Hydropathic complementarity determines interaction of epitope (869) HITDTNNK(876) in *Manduca sexta* Bt-R(1) receptor with loop 2 of domain 11 of *Bacillus thuringiensis* CryI A toxins. J. Biol. Chem_ 277, 30137-30143.

Hua, G., Jurat-Fuentes, Adang, M. J., 2004. Bt-R1a extracellular cadherin repeat 12 mediates *Bacillus thuringiensis* Cryl Ab binding and toxicity. J. Biol. Chem. 279, 28051-28056.

Hua, G., Zhang, Q. Zhang, R., Abdullah, A. M., Linser, P. J., Adang, M. J., 2013. AgCad2 cadherin in *Anopheles gamhiae* larvae is a putative receptor of CryllBa toxin of *Bacillus thuringiensis* subspjegathesan. Insect Biochem. Mol. Biol. 43, 153-161.

Hua, G., Zhang, R., Abdullah, M. A., Adang, M. J., 2008. *Anopheles gambiae* cadherin A2Cad1 binds the Cry4Ba toxin of *Bacillus thuringiensis israelensis* and a fragment of AgCad 1 synergizes toxicity. Biochemistry 47, 5101-5110.

Ikawa, S., Tsuda, Y., Fukada, T., Sugimoto, K., 1-limeno, M., 2000. cDNA cloning of the Cryl Aa receptor variants from *Bombyx mori* and their expression in mammalian cells. Biosci. Biotech. Biochem. 64, 2682-2685.

Ochoa-Campuzano, C., Real, M. D., Martinez-Ramirez, A. C., Bravo, A., Rausell, C_, 2007. An ADAM metalloprotease is a Cry3Aa Bacillus thuringiensis toxin receptor. Biochem. Biophys. Res. Commun. 362, 437-442.

Pacheco, S., Gomez, I., Gill, S. S., Bravo, A., Soberon, M., 2009. Enhancement of insecticidal activity of Bacillus thuringiensis Cry1 A toxins by fragments of a toxin-binding cadherin correlates with oligomer formation. Peptides 30, 583-588.

Park, Y., Abdullah, M. A., Taylor, M. D., Rahman, K, Adang, M. J., 2009. Enhancement of Bacillus thuringiensis Cry3Aa and Cry3Bb toxicities to coleopteran larvae by a toxin-binding fragment of an insect cadherin. Appl. Environ. Microbiol. 75, 3086-3092.

Peng, D., Xu, X., Ruan, L., Yu, Z_, Sun, M., 2010. Enhancing Cry1 Ac toxicity by expression of the Helicaverpa arinigera cadherin fragment in Bacillus thuringiensis. Res. Microbial. 161, 383-389.

Rahman, K, Abdullah, M A F, Ambati, 5, Taylor, M D, Adang, M J. 2012. Differential protection of Cry1Fa toxin against Spodoptera frugiperda larval gut proteases by cadherin orthologs correlates with increased synergism. Appl. Environ. Microb. 78:354-362.

Salin, C., Delettre, Y. R., Vernon, P., 2003. Controlling the mealworm Alphitoblus diaperinus (Coleoptera: Tenebrionidae) in broiler and turkey houses: field trials with a combined insecticide treatment: insect growth regulator and pyrethroid. J. Econ. Entomol. 96, 126-130.

Schnepf, E., Crickmore, N., Van Rie, J., Lereclus, D., Baum, J., Feitelson, J., Ziegler, D. R., Dean, D. H., 1998. Bacillus thuringiensis and its pesticidal proteins. Microbial. Mol. Biol. Rev. 62, 775-806.

Shearer, L. 'UGA scientists' inventions could make world better.' 2012. OnlineAthens.com. 22 Oct. 2012. Website: onlineathens.com/local-news/2012-03-23/uga-sci entists-in v en ti ons-c ould-make-world-better-group-say s.

Swanson, S. 'Crop Protection Gets a Boost with Biotechnology.' betterwarldproject.net. Eds. N. Barman, M. Malandro. 2012. Association of University Technology Managers. 22 Oct. 2011. website: betterworldproject.arg/AM/Template.cfna? Section=PastReports& Template 4CM/ContentDisplay.cfm&Content1D=7449

Templeton, J. M., Jong, A. D., Blackall, P. J., Miflin, J K., 2006. Survival of Campylobacter spp_ in darkling beetles (Alphitobius diaperinus) and their larvae in Australia Appl. Environ. Microbial. 72, 7909-7911.

University of Georgia. "A Better World: Innovative Solutions for Global Needs.mov." 2012. YouTube.Web. 22 Oct. 2012.

Vachon, V., Laprade, R., Schwartz, J_L., 2012. Current models of the mode of action of Bacillus thuringiensis insecticidal crystal proteins: A critical review. J. Invert. Pathol. 111, 1-13.

Xie, R., Zhuang, M., Ross, L. S., Gomez, I., Oltean, D. I., Bravo, A., Soberon, M., Gill, S. S., 2005. Single amino acid mutations in the cadherin receptor from Helioihis virescens affect its toxin binding ability to Cry I A toxins. J. Biol. Chem. 280, 8416-8425.

Zhang, X., Kain, W., Wang, 13_, 2013. Sequence variation and differential splicing of the midget cadherin gene in Trichoplusia ni. Insect Biochem. Mol. Biol. 43, 712-723.

Zhang, X. B., Candas, M., Griko, N. B., Taussig, R., Bulla, J. L., 2006. A mechanism of cell death involving an adenylyl cyclase/PKA signaling pathway is induced by the Cry1 Ab toxin of Bacillus thuringiensis. Proc. Natl. Acad. Sci. U.S.A 103, 9897-9902.

Ititliga-Navarrete, F., Gomez, I., Pew, G., Bravo, A., Soberon, M., 2013. A Tenebrio molitor GPI-anchored alkaline phosphatase is involved in binding of Bacillus thuringiensis Cry3Aa to brush border membrane vesicles. Peptides 41, 81-86

What is claimed is:

1. An expression vector comprising DNA that encodes an AdCad1 fragment, wherein the AdCad1 fragment consists of: a polypeptide with at least 95% sequence identity with AdCad1-CR9 (SEQ ID NO: 4); or a polypeptide with at least 95% sequence identity with AdCad1-MPED (SEQ ID NO: 6).

2. The expression vector according to claim 1, wherein DNA encoding the AdCad1 fragment consists of a nucleic acid sequence with at least 90% sequence identity to: SEQ ID NO:3; or SEQ ID NO:5.

3. A transgenic plant comprising DNA encoding one or more AdCad1 fragments, wherein each of the one or more AdCad1 fragments consists of: a polypeptide with at least 95% sequence identity with AdCad1-CR9 (SEQ ID NO: 4); or a polypeptide with at least 95% sequence identity with AdCad1-MPED (SEQ ID NO: 6), wherein the plant is capable of expressing the one or more AdCad1 fragments.

4. The transgenic plant of claim 3, further comprising DNA encoding one or more Cry proteins selected from Cry3Bb, Cry8Ca, Cry34, and Cry35, wherein the plant is capable of expressing the one or more Cry proteins.

5. The transgenic plant of claim 3, wherein the plant is a corn plant.

6. A seed, tissue, or plant part of the transgenic plant according to claim 3.

7. A transgenic plant expressing one or more AdCad1 fragments, wherein each of the one or more AdCad1 fragments consists of: a polypeptide with at least 95% sequence identity with AdCad1-CR9 (SEQ ID NO: 4); or a polypeptide with at least 95% sequence identity with AdCad1-MPED (SEQ ID NO: 6).

8. The transgenic plant of claim 7, further expressing one or more Cry proteins selected from Cry3Bb, Cry8Ca, Cry34, and Cry35, wherein the plant is capable of expressing the one or more Cry proteins.

9. The transgenic plant of claim 7, wherein the plant is a corn plant.

10. A seed, tissue, or plant part of the transgenic plant according to claim 7.

* * * * *